US008067461B2

(12) United States Patent
Reddy et al.

(10) Patent No.: US 8,067,461 B2
(45) Date of Patent: Nov. 29, 2011

(54) 3-ACYL COUMARINS, THIOCHROMONES AND QUINOLONES AND THERAPEUTIC USES THEREOF

(75) Inventors: M. V. Ramana Reddy, Upper Darby, PA (US); E. Premkumar Reddy, Villanova, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 914 days.

(21) Appl. No.: 11/921,109

(22) PCT Filed: Jun. 2, 2006

(86) PCT No.: PCT/US2006/021389
§ 371 (c)(1),
(2), (4) Date: Nov. 27, 2007

(87) PCT Pub. No.: WO2006/132947
PCT Pub. Date: Dec. 14, 2006

(65) Prior Publication Data
US 2009/0275650 A1 Nov. 5, 2009

Related U.S. Application Data

(60) Provisional application No. 60/688,550, filed on Jun. 8, 2005.

(51) Int. Cl.
*A61K 31/35* (2006.01)
*C07D 311/12* (2006.01)
(52) U.S. Cl. ........................................ 514/457; 549/284
(58) Field of Classification Search .................. 549/284; 514/457
See application file for complete search history.

(56) References Cited

U.S. PATENT DOCUMENTS

| | | | | |
|---|---|---|---|---|
| 4,147,552 A | * | 4/1979 | Specht et al. | 430/195 |
| 4,289,844 A | * | 9/1981 | Specht et al. | 430/281.1 |
| 5,415,976 A | | 5/1995 | Ali | 430/281 |
| 5,455,143 A | | 10/1995 | Ali | 430/281 |
| 6,068,940 A | | 5/2000 | Tanaka | 428/690 |
| 2006/0211680 A1 | | 9/2006 | Tomigahara et al. | 514/217.04 |
| 2007/0232649 A1 | | 10/2007 | Reddy et al. | 514/312 |

FOREIGN PATENT DOCUMENTS

| | | |
|---|---|---|
| EP | 0565074 B1 | 8/1999 |
| WO | WO 01/17984 A1 | 3/2001 |
| WO | WO 02/098425 A1 | 12/2002 |

OTHER PUBLICATIONS

Registry No. 64267-18-1 (2002).*
Registry No. 115948-26-0 (1988).*
Registry No. 165597-49-9 (1995).*
Registry No. 64267-20-5 (1984).*

Doucet et al., "6-Substituted 2-Oxo-2H-1-benzopyran-3-carboxylic Acid as a Core Structure for Specific Inhibitors of Human Leukocyte Elastase," J. Med. Chem, vol. 42, pp. 4161-4171, 1999.
Egan et al., "The Pharmacology, Metabolism, Analysis, and Applications of Coumarin and Coumarin-Related Compounds," Drug Metabolism Reviews, vol. 22, No. 5, pp. 503-529 (1990).
Hamad et al., "Synthesis and Reactions of 3-Acetyl and 3-Cinnamoyl Coumarins," Pak. J. Sci. Ind. Res., vol. 33, No. 12, pp. 515-519, Dec. 1990.
Mor et al., "Reaction of thrombin and proteinases of the fibrinolytic system with a mechanism-based inhibitor, 3,4-dihydro-3-benzyl-6-chloromethylcourmarin," Biochimica et Biophysica Acta, vol. 1038, pp. 119-124 (1990).
Nicolaides et al., "Synthesis and Biological Evaluation of some 4-(Isoxazolinyl or 1,2,4-Oxadiazolyl) Coumarins," J. Heterocyclic Chem., vol. 33, pp. 967-971, May-Jun. 1996.
Pochet et al., "Coumarinic Derivatives as Mechanism-Based Inhibitors of α-Chymotrypsin and Human Leukocyte Elastase," Bioorganic & Medicinal Chemistry, vol. 8, pp. 1489-1501, 2000.
Reddy et al., "Novel coumarin-3-(N-aryl)carboxamides arrest breast cancer cell growth by inhibiting ErbB-2 and ERK1," Bioorganic & Medicinal Chemistry, vol. 13, pp. 3141-3147, 2005.
Vul'fson et al., "The Claisen-Schmidt Reaction With Heterocyclic Analogs of o-Hydroxiacetphenone," Chemistry of Heterocyclic Compounds, The Faraday Press, Inc., vol. 3, No. 4, pp. 546-548, Jul.-Aug. 1967.
Woods et al., "3,3'-Keto Biscoumarins," Journal of Chemical and Engineering Data, vol. 12, No. 4, pp. 624-626, Oct. 1967.
Wouters et al., "Structural Approach of the Mechanism of Inhibition of α-Chymotrypsin by Coumarins," Bioorganic & Medicinal Chemistry Letters, vol. 12, pp. 1109-1112, 2002.
Patent Abstracts of Japan, Abstract of JP01253733, 1989.
Chemical Abstracts, 76:59380, abstracting Asker et al., "Behavior of some 4-hydroxy-1-thiocoumarins toward amines and phenylhydrazine," Journal fuer Praktische Chemie (Leipzig), vol. 313, No. 4, pp. 715-721, 1971.
Chemical Abstracts, 87:192041, abstracting Specht et al., "Sensitizers for photocrosslinkable polymers," Research Disclosure, vol. 161, pp. 65-68, 1977.
Chemical Abstracts, 96:52200, abstracting El-Garby Younes et al., "Reactions of 3-acetyl-6-bromocoumarin: synthesis of 6H-1,3-benzoxazocine, 7H-[1]benzopyrano[3,4-c]quinoline, 5H-[1]benzopyrano[3,4-c]pyridine, 6H-dibenzo[b,d]pyran, xanthene and chroman derivatives," Indian Journal of Chemistry, Section B: Organic Chemistry Including Medicinal Chemistry, vol. 20B, No. 9, pp. 747-750, 1981.

(Continued)

Primary Examiner — Bernard Dentz
(74) Attorney, Agent, or Firm — Drinker Biddle & Reath LLP

(57) ABSTRACT

Compounds of Formula I:

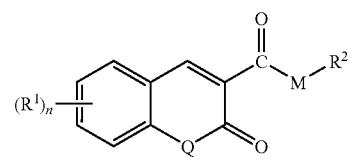

wherein $R^1$, $R^2$, M, Q and n are as defined herein, are useful as antiproliferative agents including, for example, as anticancer agents.

19 Claims, No Drawings

OTHER PUBLICATIONS

Chemical Abstracts, 97:72262, abstracting Lacan et al., "Synthesis of heretocycles bonded in site 3-, and heterocycles condensed on sites 3,4 of the coumarin nucleus," Glasnik Hemijskog Drustva Beograd, vol. 46, No. 10, pp. 531-537, 1981.

Chemical Abstracts, 97:144729, abstracting Specht et al., "Ketocoumarins. A new class of triplet sensitizers," Tetrahedron, vol. 38, No. 9, pp. 1203-1211, 1982.

Chemical Abstracts, 100:203314, abstracting Rehse et al., "Effect of S-oxidation on the anticoagulant activity of 4-hydroxycoumarins, 4-hydroxy-2-pyrones, and 1,3-indanediones," Archiv der Pharmazie (Weinheim, Germany), vol. 317, No. 3, pp. 262-267, 1984.

Chemical Abstracts, 101:90817, abstracting Raju et al., "Synthesis and antimicrobial activity of 3-(3'-coumaryl)-5-substituted phenyl-2-pyrazolines, 1-phenyl-3-(3'-coumaryl)-5-substituted phenyl-2-pyrazolines and 3-(3'-coumaryl)-5-substituted phenyl-2-isoxazolines," Acta Ciencia Indica, Chemistry, vol. 9, No. 1-4, pp. 168-171, 1983.

Chemical Abstracts, 102:113224, abstracting Van den Goorbergh et al., "A convenient synthesis of 3-(1-oxo-2-alkenyl)coumarins," Synthesis, No. 10, pp. 859-860, 1984.

Chemical Abstracts, 104:188143, abstracting Chandrasekhar et al., "Synthesis of biscoumarins and biscoumarinyl ketones," Dyes and Pigments, vol. 7, No. 1, pp. 13-21, 1986.

Chemical Abstracts, 106:119621, abstracting Dimitrova et al., "Condensation of 3-acetyl- and 3-acetyl-4-methyl-2H-1-benzopyran-2-one with aromatic aldehydes," Synthetic Communications, vol. 16, No. 10, pp. 1195-1205 (1986).

Chemical Abstracts, 113:14881, abstracting JP 01253733, (1988).

Chemical Abstracts, 116:151531, abstracting Vostrova et al., "Synthesis and properties of new $\alpha,\beta$-unsaturated ketones derived from substituted 2-quinolones," Ukrainskii Khimicheskii Zhurnal (Russian Edition), vol. 57, No. 10, pp. 1115-1118, 1991.

Chemical Abstracts, 116:194440, abstracting Yagodinets et al., "Synthesis and study of acyl phospholium compounds of coumarin," Zhurnal Obshchei Khimii, vol. 61, No. 8, pp. 1856-1862, 1991.

Chemical Abstracts, 117:131114, abstracting Osman et al., "Cinnamoylacetonitrile in organic synthesis," Egyptian Journal of Chemistry, Vo. 31, No. 6, pp. 743-750, 1990.

Chemical Abstracts, 122:119141, abstracting JP 06175557, (1992).

Chemical Abstracts, 123:313684, abstracting Yagodinets et al., "Phosphorus-containing derivatives of 6-(phenylazo)coumarin," Zhurnal Obshchei Khimii, vol. 65, No. 2, pp. 334, 1995.

Chemical Abstracts, 124:232247, abstracting JP 07267942, (1994).

Chemical Abstracts, 124:232249, abstracting JP 07316147, (1994).

Chemical Abstracts, 125:25610, abstracting Oganesian et al., "Electronic structure-activity relationship (ESAP) in propene derivatives. 1,4-Carboxyvinylenechalcones and 3-cinnamoylcoumarins," Khimiko-Farmatsevticheskii Zhurnal, vol. 28, No. 11, pp. 36-39, 1994.

Chemical Abstracts, 127:161741, abstracting Miky et al., "Synthesis and reactions of 3-cinnamoycoumarin derivatives with activated nitriles," Indian Journal of Chemistry, Section B: Organic Chemistry Including Medicinal Chemistry, vol. 36B, No. 4, pp. 357-360, 1997.

Chemical Abstracts, 127:248874, abstracting JP 09227547, (1996).

Chemical Abstracts, 127:263186, abstracting JP 09221486, (1996).

Chemical Abstracts, 130:238777, abstracting Tsatsaroni et al., "Synthesis and characterization of 3-ketocoumarins: substituent effects on color," Journal of the Society of Dyers and Colourists, vol. 115, No. 2, pp. 62-68, 1999.

Chemical Abstracts, 134:208445, abstracting Creed et al., "Triplet-sensitized irradiation of a main-chain liquid crystalline poly(aryl cinnamate) in three different phases," Journal of Polymer Science, Part A: Polymer Chemistry, vol. 39, No. 1, pp. 134-144, 2001.

Chemical Abstracts, 136:401624, abstracting Ol'khovik et al., "Synthesis and properties of 3-cinnamoyl-4-hydroxy-3-quinolone," Russian Journal of General Chemistry, vol. 71, No. 8, pp. 1257-1260, 2001.

Chemical Abstracts, 137:241666, abstracting Woulters et al., "Structural approach of the mechanism of inhibition of $\alpha$-chymotrypsin by coumarins,", Bioorganic & Medicinal Chemistry Letters, vol. 12, No. 7, pp. 1109-1112, 2002.

Chemical Abstracts, 140:253404, abstracting Stanciu et al., "Synthesis and reactivity of some 3-cinnamoylcoumarin derivatives," Analele Stiintifice ale Universitatii "Al. I. Cuza" din. Iasi, Chimie, vol. 10, No. 2, pp. 287-290, 2002.

Chemical Abstracts, 140: 332530, abstracting JP 2004123620, (2002).

Chemical Abstracts, 140:350621, abstracting JP 2004123621, (2002).

Chemical Abstracts, 141:7477, abstracting Wang et al., "Synthesis of novel ketocoumarin visible-light photosensitive dye and its initiating properties," Huaxue Xuebao, vol. 63, No. 5, pp. 527-531, 2004.

CASREACT database, abstracting 2-step condensation-cyclization, Indian Journal of Chemisty, Section B: Organic Chemistry Including Medicinal Chemistry, vol. 26B, No. 5, pp. 427-430, 1987.

Trenknerowna, M., (Abstract of) *Roczniki Chemii*, (1936) vol. 16, p. 12-18; CAS Online-RN 873972-89-5 and 873972-87-3, CA 31:15845 (1937).

Trenknerowna, M., (Abstract of) *Roczniki Chemii*, (1936) vol. 16, p. 6-10; CAS Online-RN 857783-01-8, CA 31:15844 (1937).

Lampe et al., (Abstract of) *J. Compte Rend. Soc. Sci. letters Varsovie*, (1938), vol. 31 (Classe III), p. 63-65; CAS Online, RN 855158-48-4, 855574-31-3, 855159-69-2, 854643-03-1, 854403-17-1 CA 36:41260 (1942).

Rakower (Abstract of) *Acta Phys. Polonica*, (1934) vol. 3, p. 415-420; CAS Online, RN 854643-01-9, CA 31:15285 (1937).

Lampe et al., (Abstract of) *Roczniki Chemii*, (1938) vol. 18, p. 668-679; CAS Online, RN 855159-33-0, CA 34:18347 (1940).

* cited by examiner

3-ACYL COUMARINS, THIOCHROMONES AND QUINOLONES AND THERAPEUTIC USES THEREOF

FIELD OF THE INVENTION

The invention relates to 3-acyl coumarins, thiochromones and quinolones. The invention further relates to pharmaceutical compositions containing such compounds, and to methods of treatment comprising administration of such compounds.

BACKGROUND OF THE INVENTION

A. Biological Activity of Coumarin Derivatives

Anticoagulant and antithrombotic activity of certain natural and synthetic coumarin derivatives is known. See, Murray et al., *The Natural Coumarins*, Wiley, New York, 1982. Certain coumarin derivatives are also reported as triplet sensitizers (see, Williams et al., *Polym. Eng. Sci.*, 1983, 23, 1022); anti-HIV agents (Spino et al., *Bioorg. Med. Chem. Lett.*, 1998, 8, 3475-78); lipid-lowering agents (Madhavan et al., *Bioorg. Med. Chem. Lett.*, 2003, 13, 2547-51); antioxidants (Kontogiorgis et al., *J. Enzyme Inhib. Med. Chem.*, 2003, 18, 63-69); inhibitors of lipid peroxidation and vasorelaxant agents (Hoult et al., *Gen. Pharmac.* 1996, 27, 713-22); anti-inflammatory agents (Khan et al., *Indian J. Chem.*, 1993, 32, 817); and free radical scavengers (Mora et al., *J. Biochem. Pharmacol.*, 1990, 40, 793-97). In addition, two naturally-occurring coumarins have been found to exhibit cytotoxicity across a selection of mammalian cancer cell lines (Reutrakul et al., *Planta Med.*, 2003, 69, 1048-51).

Certain coumarin-3-carboxamides have been reported as inhibitors of proteases, including α-chymotrypsin (Pochet et al., *Bioorg. Med. Chem. Lett.*, 2000, 8, 1489-501; Wouters et al., *Bioorg. Med. Chem. Lett.*, 1990, 12, 1109-12; and Mor et al., *Biochim. Biophys. Acta*, 1990, 1038, 119-24) and human leukocyte elastase (HLE) (Doucet et al., *J. Med. Chem.*, 1999, 42, 4161-71; Egan et al., *Drug Metab. Rev.*, 1990, 22, 503-29; and Nicolaides et al., *J. Heterocycl. Chem.*, 1996, 33, 967).

B. Cyclin Dependent Kinase (CDK) Inhibition

One of the most important and fundamental processes in biology is the division of cells mediated by the cell cycle. The cell cycle is regulated by a diverse set of cellular signals both within the cell and from external sources. A complex network of tumor promoting and suppressing gene products are key components of this cellular signaling process. Overexpression of the tumor promoting components or the subsequent loss of the tumor suppressing products may lead to unregulated cellular proliferation and the generation of tumors. CDKs serve to regulate the cell cycle. CDK complexes comprise a catalytic subunit (the kinase) and a regulatory subunit (the cyclin). Nine kinase subunits (CDK 1-9) have been identified along with several regulatory subunits (cyclins A-H).

CDKs are important targets for therapeutic intervention in various proliferative disorders including cancer. Each kinase associates with a specific regulatory partner and together make up the active catalytic moiety. Each transition of the cell cycle is regulated by a particular CDK complex. The coordinated activity of these kinases guides the individual cells through the replication process and ensures the vitality of each subsequent generation.

Overexpression of the cyclin regulatory proteins and subsequent kinase hyperactivity have been linked to several types of cancers (Jiang, *Proc. Natl. Acad. Sci. USA* 90:9026-9030, 1993; Wang, *Nature* 343:555-557, 1990). Endogenous CDK inhibitors (e.g., p16$^{INK4}$ (an inhibitor of CDK4/D1), p21$^{CIP1}$ (a general CDK inhibitor), and p27$^{KIP1}$ (a specific CDK2/E inhibitor) have been shown to affect cellular proliferation (Kamb et al., *Science* 264:436-440, 1994; Beach, *Nature* 336:701-704, 1993). These inhibitors help to regulate the cell cycle through specific interactions with their corresponding CDK complexes. Cells deficient in these inhibitors are prone to unregulated growth and tumor formation. CDKs are also known to play a role in apoptosis.

New CDK inhibitors, particularly small molecule inhibitors, would be useful in the treatment of cell proliferative disorders such as cancer, familial adenomatosis polyposis, neuro-fibromatosis, psoriasis, fungal infections, endotoxic shock, transplantation rejection, vascular smooth cell proliferation associated with atherosclerosis, pulmonary fibrosis, arthritis glomerulonephritis and post-surgical stenosis and restenosis. U.S. Pat. No. 6,114,365 discloses that CDK inhibitors are useful in the treatment of cancers that include carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma. See, U.S. Pat. No. 6,114,365, the entire disclosure of which is incorporated herein by reference.

Cell cycle control is also implicated in viral replication. CDK9 is known to activate Tat, a nuclear transcriptional activator encoded by Human Immunodeficiency Virus (HIV). HIV type 1 (HIV-1) can infect quiescent cells. However, viral production is restricted to actively proliferating cells. The HIV-1 viral protein Tat acts to perturb the cell cycle thereby optimizing HIV-1 replication. Tat regulates the cell cycle by altering factors involved in proliferation and differentiation, and by associating with cyclin/CDK complexes.

Tat protein is a potent activator of HIV-1 transcription that functions at an early step in elongation. Tat acts to enhance the processivity of RNA polymerase II (RNAPII) complexes that would otherwise terminate transcription prematurely at random locations downstream of the viral RNA start site. The mechanism of Tat transactivation is unique in that the cis-acting transactivation response element (TAR) is a stable RNA stem-loop structure that forms at the 5' end of nascent viral transcripts. Transcriptional activation by Tat through TAR requires proper folding of the RNA as well as specific bases in the bulge and apical loop of the TAR RNA hairpin structure. See, Cullen, *Cell* 73:417-420 (1993) and Jones et al., *Ann. Rev. Biochem.* 63:717-743 (1994) the entire disclosures of which are incorporated herein by reference.

The role for CDK9 in Tat transactivation has been shown in random drug screens for specific inhibitors of Tat, which yield novel compounds directed against the active site of CDK9 (Mancebo et al. (1997) *Genes Dev* 11:2633-2644). In addition a dominant negative mutant CDK9 protein has been shown to block Tat activity in vivo (Id.; Yang et al. (1997) *Proc. Natl. Acad. Sc. USA* 94:12331-12336). Thus, inhibitors of CDK9 represent a means to treat viral infection by inhibiting viral replication. Inhibition of CDK9 has also been shown to inhibit replication of other viruses including varicella-zoster virus and herpes simplex. See, Taylor et al., J. Virol., 78(6), page 2853-62 (2004), the entire disclosure of which is incorporated herein by reference.

Cancer and other proliferative disorders remain a major unmet medical need. Cancer treatments often comprise surgery, chemotherapeutic treatments, radiation treatment or combinations thereof. Chemotherapeutic treatments for most cancers only delay disease progression rather than providing a cure. Cancers often become refractory to chemotherapy via development of multidrug resistance. Particular cancers are inherently resistant to some classes of chemotherapeutic agents. See, DeVita et al, "Principles of Cancer Management: Chemotherapy" In: *Cancer. Principles and Practice of Oncology*, 5th edition, Lippincott-Raven, Philadelphia, New York (1977), pp. 333-347.

Viral infection represents another area of major unmet medical need. Viruses often develop resistance. Present therapies often demonstrate significant toxicity at therapeutic doses, and even then serve only to slow progression of the viral disorder.

Thus, there remains a need to develop new therapeutic agents. Oncoproteins in general, and signal transducing proteins, such as CDKs in particular, are likely to be more selective targets for chemotherapy because they represent a subclass of proteins whose activities are essential for cell proliferation, and because their activities are greatly amplified in proliferative diseases.

DEFINITIONS

General

The term "individual" includes human beings and non-human animals.

The expression "effective amount" when used to describe therapy to an individual suffering from a cancer or other disorder which manifests abnormal cellular proliferation, refers to the amount of a compound according to Formula I that inhibits the growth or proliferation of tumor cells, or alternatively induces apoptosis of cancer cells, preferably tumor cells, resulting in a therapeutically useful and preferably selective cytotoxic effect on proliferative cells.

The expression "effective amount" when used to describe therapy to an individual suffering from HIV, or other viral disorder, refers to the amount of a compound according to Formula I that inhibits the replication of the virus, resulting in a therapeutically useful effect on a viral infection of the individual.

The term "proliferative disorder" means a disorder wherein cells are made by the body at an atypically accelerated rate.

Chemical

The term "alkyl", by itself, or as part of another substituent, e.g., haloalkyl or aminoalkyl, means, unless otherwise stated, a saturated hydrocarbon radical having the designated number of carbon atoms (i.e. $C_1$-$C_6$ means the group contains one, two, three, four, five or six carbons) and includes straight, branched chain, cyclic and polycyclic groups. Examples include methyl, ethyl, propyl, isopropyl, butyl, isobutyl, tert-butyl, pentyl, neopentyl, hexyl, cyclohexyl, norbornyl and cyclopropylmethyl. Preferred alkyl groups comprise —($C_1$-$C_6$)alkyl. Most preferred is —($C_1$-$C_3$)alkyl, particularly ethyl, methyl and isopropyl.

"Substituted alkyl" means alkyl, as defined above, substituted by one, two or three substituents. The substituents are preferably independently selected from the group consisting of halogen, —OH, —O($C_1$-$C_4$)alkyl, —NH$_2$, —N(CH$_3$)$_2$, —CO$_2$H, —CO$_2$($C_1$-$C_4$)alkyl, —CF$_3$, —CONH$_2$, —SO$_2$NH$_2$, —C(=NH)NH$_2$, —CN and —NO$_2$. More preferably, the substituted alkyl contains one or two substituents independently selected from the group consisting of halogen, —OH, NH$_2$, —N(CH$_3$)$_2$, trifluoromethyl and —CO$_2$H; most preferably, halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon radical having the designated number of carbons. For example, the expression "—C(=O)($C_1$-$C_4$)alkylene-R" includes one, two, three and four carbon alkylene groups. A substitution of a group such as R on alkylene may be at any substitutable carbon. For example, the group, -(=O)($C_4$ alkylene)R, includes, for example (a), (b) and (c), in Scheme 1, below:

Scheme 1

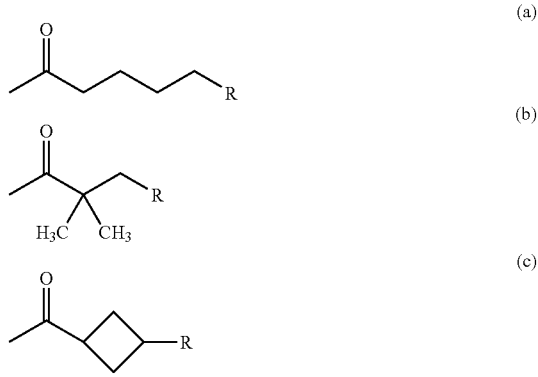

The term "amine" or "amino" refers to radicals of the general formula NRR', wherein R and R' are independently hydrogen or a hydrocarbyl radical, or wherein R and R' combined form a heterocycle. Examples of amino groups include —NH$_2$, methyl amino, diethyl amino, anilino, benzyl amino, piperidinyl, piperazinyl and indolinyl.

The term "aromatic" refers to a carbocycle or heterocycle having one or more polyunsaturated rings having aromatic character (4n+2) delocalized π (pi) electrons).

The term "aryl", employed alone or in combination with other terms, means, unless otherwise stated, a carbocyclic aromatic group containing one or more rings (typically one, two or three rings) wherein such rings may be attached together in a pendent manner, such as a biphenyl, or may be fused, such as naphthalene. Examples include phenyl, anthracyl and naphthyl. Preferred are phenyl and naphthyl, most preferred is phenyl.

The term "aryl-($C_1$-$C_3$)alkyl" means a radical wherein a one to three carbon alkylene chain is attached to an aryl group, e.g., —CH$_2$CH$_2$-phenyl. Preferred are aryl(CH$_2$)— and aryl (CH(CH$_3$))—. The term "substituted aryl-($C_1$-$C_3$)alkyl" means an aryl-($C_1$-$C_3$)alkyl radical in which the aryl group is substituted. Preferred is substituted aryl(CH$_2$)—. Similarly, the term "heteroaryl($C_1$-$C_3$)alkyl" means a radical wherein a one to three carbon alkylene chain is attached to a heteroaryl group, e.g., —CH$_2$CH$_2$-pyridyl. Preferred is heteroaryl (CH$_2$)—. The term "substituted heteroaryl-($C_1$-$C_3$)alkyl" means a heteroaryl-($C_1$-$C_3$)alkyl radical in which the heteroaryl group is substituted. Preferred is substituted heteroaryl(CH$_2$)—.

The term "arylene", by itself or as part of another substituent means, unless otherwise stated, a divalent aryl radical. Preferred are divalent phenyl radicals, particularly 1,4-divalent phenyl radicals.

The term "coumarin", by itself, or as part of a larger chemical name, means, unless otherwise stated, a bicyclic heteroaryl ring system of the Formula:

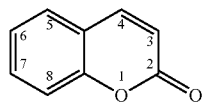

wherein the numbering of the positions in the bicyclic heteroaryl ring is as shown. Alternative naming of coumarin compounds includes nomenclature such as "2H-chromene-2-one" and "2H-benzopyran-2-one". Specific compounds herein are named as 2H-chromene-2-ones.

The term "thiochromene-2-one", by itself, or as part of a larger chemical name, as employed herein means, unless otherwise stated, a bicyclic heteroaryl ring system of the Formula:

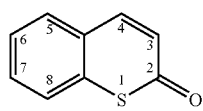

wherein the numbering of the positions in the bicyclic heteroaryl ring is as shown.

The term "2-quinolone", by itself, or as part of a larger chemical name, as employed herein means, unless otherwise stated, a bicyclic heteroaryl ring system of the Formula:

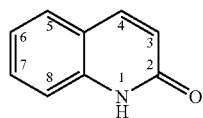

wherein the numbering of the positions in the bicyclic heteroaryl ring is as shown. The 2-quinolone exists in a plurality tautomeric forms:

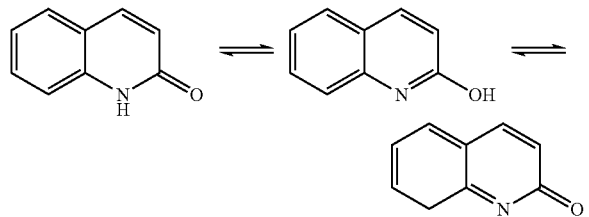

both of which are understood to be included within the term 2-quinolone.

The term "cycloalkyl" refers to ring containing alkyl radicals Examples include cyclohexyl, cyclopentyl, cyclopropyl methyl and norbornyl.

The term "hydrocarbyl" refers to any moiety comprising only hydrogen and carbon atoms. Such as, for example aryl, alkyl, alkenyl and alkynyl groups. Preferred hydrocarbyl groups are $(C_1-C_{12})$hydrocarbyl, more preferred are $(C_1-C_8)$ hydrocarbyl, most preferred are phenyl, benzyl and —$(C_1-C_6)$alkyl.

The term "hydrocarbylene" by itself or as part of another substituent means, unless otherwise stated, a divalent moiety comprising only hydrogen and carbon atoms. A substitution of another group —R on hydrocarbylene may be at any substitutable carbon, i.e., the expression —$(C_1-C_6$ hydrocarbylene)R includes, for example, the structures shown in Scheme 2:

Scheme 2

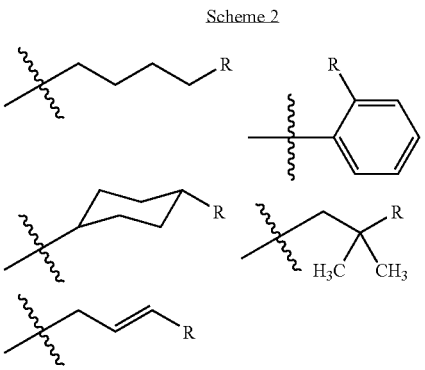

The term "heteroalkyl" by itself or in combination with another term means, unless otherwise stated, a stable straight or branched chain radical consisting of the stated number of carbon atoms and one or two heteroatoms selected from the group consisting of O, N, and S, wherein the sulfur heteroatoms may be optionally oxidized and the nitrogen heteroatoms may be optionally quaternized or oxidized. The oxygens bonded to oxidized sulfur or nitrogen may be present in addition to the one or two heteroatoms in the heteroalkyl group. The heteroatom(s) may occupy any position in the heteroalkyl group, including the attachment position of the heteroalkyl group and a terminal atom of the heteroalkyl group. Examples of heteroalkyl groups include: —S—CH$_2$—CH$_2$—CH$_3$, —CH$_2$—CH$_2$CH$_2$—OH, —CH$_2$—CH$_2$—NH—CH$_3$, —CH$_2$—SO$_2$—NH—CH$_3$, —CH$_2$—S—CH$_2$—CH$_3$ and —CH$_2$CH$_2$—S(=O)—CH$_3$. Two heteroatoms may be bonded to each other, such as, for example, —CH$_2$—NH—OCH$_3$, or —CH$_2$—CH$_2$—S—S—CH$_3$.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from the group consisting of N, O, and S, wherein the nitrogen and sulfur heteroatoms may be optionally oxidized, and the nitrogen atom may be optionally quaternized. Unless otherwise stated, a heterocycle may be attached to a compound of which it is a component, at any heteroatom or carbon atom in the heterocycle which affords a stable structure.

The term "heteroaryl" or "heteroaromatic" refers to a heterocycle having aromatic character. A monocyclic heteroaryl group is preferably a 5-, 6-, or 7-membered ring, examples of which are pyrrolyl, furyl, thienyl, pyridyl, pyrimidinyl and pyrazinyl. A polycyclic heteroaryl may comprise multiple aromatic rings or may include one or more rings which are partially saturated.

Examples of polycyclic heteroaryl groups containing a partially saturated ring include 1,2,3,4-tetrahydroquinolyl, 1,2,3,4-tetrahydroisoquinolyl, indolinyl, 2,3-dihydrobenzofuryl and dihydrocoumarinyl. For compounds according to the invention, the attachment point on the aromatic group $R^2$ is understood to be on an atom which is part of an aromatic monocyclic ring or a ring component of a polycyclic aromatic which is itself an aromatic ring. For example, on the partially saturated heteroaryl ring 1,2,3,4-tetrahydroisoquinoline, attachment points are ring atoms at the 5-, 6-, 7- and 8-positions. The attachment point on aromatic group $R^2$ may be a ring carbon or a ring nitrogen and includes attachment to form aromatic quaternary ammonium salts such as pyridinium.

Examples of non-aromatic heterocycles include monocyclic groups such as: aziridinyl, oxiranyl, thiiranyl, azetidinyl, oxetanyl, thietanyl, pyrrolidinyl, pyrrolinyl, imidazolinyl, pyrazolidinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, 1,4-dihydropyridinyl, piperazinyl, morpholinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepinyl, 4,7-dihydro-1,3-dioxepinyl and hexamethyleneoxide.

Examples of monocyclic heteroaryl groups include, for example, six-membered monocyclic aromatic rings such as, for example, pyridyl, pyrazinyl, pyrimidinyl and pyridazinyl; and five-membered monocyclic aromatic rings such as, for example, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: indolyl, indolinyl, quinolyl, tetrahydroquinolyl, isoquinolyl, 1,2,3,4-tetrahydroisoquinolyl, cinnolinyl, quinoxalinyl, quinazolinyl, phthalazinyl, 1,8-naphthyridinyl, 1,4-benzodioxanyl, chromene-2-one-yl (coumarinyl), dihydrocoumarin, chromene-4-one-yl, benzofuryl, 1,5-naphthyridinyl, 2,3-dihydrobenzofuryl, 1,2-benzisoxazolyl, benzothienyl, benzoxazolyl, benzthiazolyl, purinyl, benzimidazolyl, benztriazolyl, thioxanthinyl, benzazepinyl, benzodiazepinyl, carbazolyl, carbolinyl, acridinyl, pyrrolizidinyl and quinolizidinyl.

The term "heteroarylene", by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from the group consisting of pyridine, piperazine, pyrimidine, pyrazine, furan, thiophene, pyrrole, thiazole, imidazole and oxazole.

The aforementioned listing of heterocyclyl and heteroaryl moieties is intended to be representative, not limiting.

The terms "halo" or "halogen" by themselves or as part of another substituent, e.g., "haloalkyl", mean, unless otherwise stated, a fluorine, chlorine, bromine, or iodine atom. Fluorine, chlorine and bromine are preferred. Fluorine and chlorine are most preferred.

The term "haloalkyl" means, unless otherwise stated, an alkyl group as defined herein containing at least one halogen substituent and no substituent that is other than halogen. Multiple halogen substituents, up to substitution of all substitutable hydrogens on the alkyl group are possible. The halogen substituents may be the same or different. Preferred haloalkyl groups include, for example, perfluoro($C_1$-$C_6$)alkyl, trifluoro($C_1$-$C_6$)alkyl, gem-difluoro($C_1$-$C_4$)alkyl and chloro($C_1$-$C_4$)alkyl. More preferred haloalkyl groups include, for example, —$CF_3$, —$C_2F_5$, —$CH_2CF_3$, —$CHF_2$, $CF_2CH_3$ and —$CH_2Cl$.

The term "($C_x$-$C_y$)perfluoroalkyl", wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "trifluoro($C_x$-$C_y$)alkyl" means an alkyl group with a minimum of x carbon atoms and a maximum of y carbon atoms, wherein the three hydrogen atoms on a terminal carbon (—$CH_3$) are replaced by fluorine atoms. Examples include —$CH_2CF_3$, —$(CH_2)_2$—$CF_3$ and —$CH(CH_3)$—$CF_3$.

The term "gem-difluoro($C_x$-$C_y$)alkyl" means an alkyl group with a minimum of x carbon atoms and a maximum of y carbon atoms, wherein one carbon atom is geminally substituted with two fluorine atoms. The fluorine-substituted carbon may be any carbon in the chain having at least two substitutable hydrogens, including the terminal —$CH_3$ group and the proximal carbon through which the difluoro($C_x$-$C_y$)alkyl is bonded to the rest of the molecule. Examples include —$CH_2CF_2H$, —$(CH_2)_2$—$CF_2H$ and —$CF_2$—$CH_3$ and 3,3-difluorocyclohexyl.

The term "substituted" with respect to a molecule or a chemical group means that an atom or group of atoms has replaced hydrogen as the substituent attached to another group. For aryl and heteroaryl groups, the term "substituted" includes any level of substitution, namely mono-, di, tri-, tetra-, or penta-substitution, where such substitution is permitted. The substituents are independently selected, and substitution may be at any chemically accessible position.

The naming of compounds disclosed herein was done by employing the structure naming programs included in CHEMDRAW ULTRA Version 8.0© (1985-2003, CambridgeSoft Corporation, 100 Cambridgepark Drive, Cambridge, Mass. 02140 USA).

SUMMARY OF THE INVENTION

It is an object of the invention to provide compounds, compositions and methods for the treatment of cancer and other proliferative disorders and for the treatment of HIV and other viral disorders. The biologically active compounds are in the form of 3-acylcoumarins, 3-acylthiochromene-2-ones, and 3-acyl-2-quinolones.

I. Compounds According to the Invention

According to one embodiment of the invention, novel compounds are provided according to Formula I:

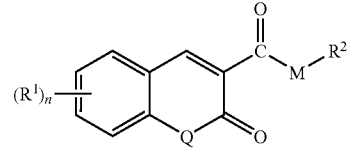

wherein:

each Q is independently O, S, or NH;

each $R^1$ is independently selected from the group consisting of halogen, —($C_1$-$C_8$)hydrocarbyl, —C(=O)$R^y$, —$NR^w{}_2$, —N($R^w$)CH($R^z$)C(=O)$R^y$, —N($R^w$)$SO_2R^y$, —N($R^w$)($C_1$-$C_4$)alkylene—$CO_2R^w$, —$NO_2$, —CN, —$OR^w$, —OC(=O)$R^y$, —OCH($R^z$)C(=O)$R^y$, —$OSO_2R^y$—O($C_1$-$C_4$)alkylene-$CO_2R^w$, —OP(=O)($OR^w$)$_2$, —O($C_2$-$C_6$)alkylene-N($CH_3$)$_2$, —O($C_1$-$C_6$)haloalkyl, —P(=O)($OR^w$)$_2$, —$SO_2$N($R^w$)$R^x$, —NHC(=NH)$NHR^x$, —($C_1$-$C_6$)haloalkyl and heteroalkyl;

$R^w$ is —H or —($C_1$-$C_8$)hydrocarbyl;

$R^x$ is —H, —($C_1$-$C_8$)hydrocarbyl or —C(=O)($C_1$-$C_8$)hydrocarbyl;

$R^y$ is selected from the group consisting of —H, —($C_1$-$C_8$)hydrocarbyl, —O($C_1$-$C_8$)hydrocarbyl, substituted phenyl, substituted heterocyclyl($C_1$-$C_3$)alkyl, heteroaryl($C_1$-$C_3$)alkyl, —$C_2$-$C_{10}$)heteroalkyl, —($C_1$-$C_6$)haloalkyl, —CH($R^z$)NHR$^x$, —N(R$^w$)R$^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$-$C_3$)alkyleneN$^+$($C_1$-$C_3$)$_3$, —($C_1$-$C_3$)alkylene-N$^+$(CH$_2$CH$_2$OH)$_3$, —($C_1$-$C_3$)alkylene-OR$^x$, —($C_1$-$C_4$)alkylene-CO$_2$R$^x$, —($C_1$-$C_4$)alkylene-CO$_2$N(R$^w$)R$^x$, —($C_1$-$C_4$)alkylene-C(=O)halogen, halo($C_1$-$C_3$)alkyl and —($C_1$-$C_4$)perfluoroalkylene-CO$_2$R$^x$;

$R^z$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently selected from the group consisting of 0, 1, 2, 3 and 4; preferably 1, 2, 3 and 4; more preferably 1, 2 and 3;

M is selected from the group consisting of a single bond and (a), (b), and (c):

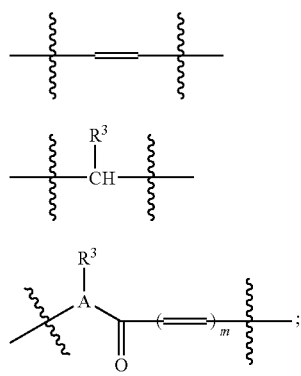

A is N or CH;

$R^2$ is substituted or unsubstituted aryl other than unsubstituted phenyl, preferably substituted aryl, more preferably substituted phenyl; or $R^2$ is substituted or unsubstituted heteroaryl, preferably monocyclic or bicyclic heteroaryl, more preferably 5- or 6-membered ring monocyclic heteroaryl or a 9- or 10-membered bicyclic heteroaryl;

$R^3$ is selected from the group consisting of —H and —($C_1$-$C_6$)alkyl, preferably —H and —CH$_3$, more preferably —H; and m is 0 or 1;

provided that:

(i) when M is a single bond, then $R^2$ is:

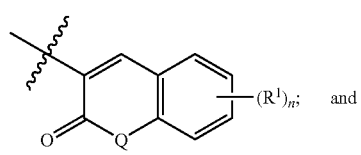

$R^1$ is other than 7-NR$^w$$_2$, or 7-OR$^w$;

(ii) when M is a single bond, and Q is O, then $R^1$ is other than:
5- or 7-halogen,
5- or 7-($C_1$-$C_8$)hydrocarbyl,
5- or 7-NO$_2$, or
5-OR$^w$;

(iii) when M is a single bond, Q is O, and n is 1, then $R^1$ is other than 6-NO$_2$, 6-Cl or 6-Br;

(iv) when M is (c) and m is 0, then $R^2$ is:

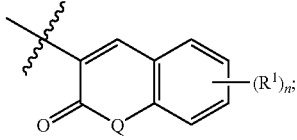

(v) when M is (b), then n is other than 0, $R^1$ is other than 7-NR$^w$$_2$, and
$R^2$ is other than 4-alkoxyphenyl;

(vi) when M is (a) and Q is O, then $R^1$ is other than —NR$^w$$_2$ and n is other than 0; and (vii) when M is (a), Q is S, and n is 1, then $R^1$ is other than 7-OR$^w$ or 7-NR$^w$$_2$;

or a salt, preferably a pharmaceutically-acceptable salt, of such a compound.

According to some embodiments, Q is O. According to other embodiments, Q is S. According to still other embodiments, Q is NH. According to other embodiments, Q is independently S or O. According to still other embodiments, Q is independently O or NH.

According to some embodiments of the invention, R$^w$ is —H. According to other embodiments of the invention, R$^w$ is —($C_1$-$C_8$)hydrocarbyl.

According to some embodiments, aryl and heteroaryl groups comprising $R^2$ are substituted by one, two or three substituents. Substituents on $R^2$ are preferably independently selected from the group consisting of halogen, —($C_1$-$C_8$)hydrocarbyl, —C(=O)R$^y$, —NR$^w$$_2$, —N(R$^w$)C(=O)R$^y$, —N(R$^w$)CH(R$^z$)C(=O)R$^y$, —N(R$^w$)SO$_2$R$^y$, —N(R$^w$)($C_1$-$C_4$)alkylene-CO$_2$R$^w$, —NO$_2$, —CN, —OR$^w$, —OC(=O)R$^y$, —OCH(R$^z$)C(=O)R$^y$, —OSO$_2$R$^y$—O($C_1$-$C_4$)alkylene-CO$_2$R$^w$, —OP(=O)(OR$^w$)$_2$, —O($C_2$-$C_6$)alkylene-N(CH$_3$)$_2$, —O($C_1$-$C_6$)haloalkyl, preferably —OCF$_3$, —P(=O)(OR$^w$)$_2$, —SO$_2$N(R$^w$)R$^x$, —NHC(=NH)NHR$^x$, —($C_1$-$C_6$)haloalkyl and heteroalkyl. More preferably, the substituents are independently selected from the group consisting of halogen, —($C_1$-$C_8$)hydrocarbyl, —C(=O)R$^y$, —NR$^w$$_2$, —NHC(=O)R$^y$, —NHC(R$^z$)C(=O)R$^y$, —NHSO$_2$R$^y$, —NH($C_1$-$C_4$)alkylene-CO$_2$R$^x$, —NO$_2$, —CN, —OR$^w$, —OC(=O)R$^y$, —OCH(R$^z$)C(=O)R$^y$, —OSO$_2$R$^y$—O($C_1$-$C_4$)alkylene-CO$_2$R$^w$, —OP(=O)(OR$^w$)$_2$, —O($C_2$-$C_6$)alkylene-N(CH$_3$)$_2$, —O($C_1$-$C_6$)haloalkyl, —P(=O)(OR$^w$)$_2$, —SO$_2$NHR$^x$, —NHC(=NH)NHR$^x$, —($C_1$-$C_6$)haloalkyl and heteroalkyl. Even more preferably, the substituents are independently selected from the group consisting of fluorine, chlorine, bromine, —($C_1$-$C_8$)hydrocarbyl, —C(=O)R$^y$, —NR$^w$$_2$, —NHC(=O)R$^y$, —NHCH(R$^z$)C(=O)R$^y$, —OCH(R$^z$)C(=O)R$^y$, —OC(=O)R$^y$, —NH($C_1$-$C_4$)alkylene-CO$_2$R$^x$, —NO$_2$, —CN, —OR$^w$, —O($C_2$-$C_6$)alkylene-N(CH$_3$)$_2$, —CF$_3$ and —OCF$_3$.

According to still other embodiments, aryl and heteroaryl groups comprising $R^2$ are substituted by one, two or three substituents that are preferably independently selected from the group consisting of fluorine, chlorine, bromine, —($C_1$-$C_8$)hydrocarbyl, —C(=O)R$^y$, —NH$_2$, —OC(=O)R$^y$ and —OR$^w$.

According to still other embodiments, aryl and heteroaryl groups comprising $R^2$ are substituted by one, two or three substituents that are —OR$^w$.

According to some embodiments, substituents on phenyl or six-membered heteroaryl $R^2$ groups are at the 2-, 4- and 6-positions of the ring. According to other embodiments, substituents on phenyl or six-membered heteroaryl $R^2$ groups are at the 2- and 4-positions of the ring. According to still other embodiments, substituents on phenyl or six-membered heteroaryl $R^2$ groups are at the 2- and 6-positions of the ring. According to still other embodiments, a single substituent on a phenyl or six-membered heteroaryl $R^2$ group is at the 2- or 4-position of the ring.

Substituents on substituted phenyl $R^y$ are preferably selected from the group consisting of —$NH_2$, —$NO_2$, N-methylpiperazinyl and —$OR^x$.

Substituents on substituted heterocyclyl($C_1$-$C_3$)alkyl groups $R^y$ are preferably —($C_1$-$C_7$)hydrocarbyl or —C(=O)($C_1$-$C_7$)hydrocarbyl; more preferably —($C_1$-$C_6$)alkyl or —C(=O) ($C_1$-$C_6$)alkyl.

According to some embodiments of the invention, each $R^1$ is independently selected from the group consisting of halogen, —($C_1$-$C_8$)hydrocarbyl, —C(=O)$R^y$, —$NR^w_2$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —CN, —$OR^w$, —OC(=O)$R^y$, —OCH($R^z$)C(=O)$R^y$, —$OSO_2R^y$—O($C_1$-$C_4$)alkylene-$CO_2R^w$, —OP(=O)(O$R^w$)$_2$, —O($C_2$-$C_6$)alkylene-N($CH_3$)$_2$, —O($C_1$-$C_6$)haloalkyl, —P(=O)(O$R^w$)$_2$, —NHC(=NH)$NHR^x$, —($C_1$-$C_6$)haloalkyl and heteroalkyl;

According to other embodiments of the invention, each $R^1$ is independently selected from the group consisting of halogen, —($C_1$-$C_8$)hydrocarbyl other than —($C_1$-$C_6$)alkyl, —C(=O)$R^y$, —$NHR^w$, —NHC(=O)$R^y$, —N($R^w$)CH($R^z$)C(=O)$R^y$, —$NHSO_2R^y$, —NH($C_1$-$C_4$)alkylene-$CO_2R^x$, —CN, —$OR^w$, —OCH($R^z$)C(=O)$R^y$, —OC(=O)$R^y$, —O($C_1$-$C_6$)haloalkyl, —P(=O)(O$R^w$)$_2$, —OP(=O)(O$R^w$)$_2$, —O($C_2$-$C_6$)alkylene-N($CH_3$)$_2$, —NHC(=NH)$NHR^x$, —($C_1$-$C_6$)haloalkyl and heteroalkyl.

According to still other embodiments of the invention, each $R^1$ is independently selected from the group consisting of fluoro, chloro, bromo, —($C_1$-$C_8$)hydrocarbyl, —C(=O)$R^y$, —$NHR^w$, —NHC(=O)$R^y$, —NHCH($R^z$)C(=O)$R^y$, —NH($C_1$-$C_4$)alkylene-$CO_2R^x$, —CN, —$OR^w$, —OCH($R^z$)C(=O)$R^y$, —OC(=O)$R^y$, —O($C_1$-$C_6$)haloalkyl, —O($C_2$-$C_6$)alkylene-N($CH_3$)$_2$, —OP(=O)(O$R^w$)$_2$ and —($C_1$-$C_6$)haloalkyl.

According to still other embodiments of the invention, each $R^1$ is independently selected from the group consisting of fluoro, chloro and bromo, —($C_1$-$C_6$)alkyl, —C(=O)$R^y$, —NHC(=O)$R^y$, —$NHSO_2R^y$, —CN, —OC(=O)$R^y$, —O($C_1$-$C_6$)alkyl, —OP(=O)(O$R^w$)$_2$ and —($C_1$-$C_6$)haloalkyl.

According to some embodiments of compounds according to the invention, when M is a single bond and Q is O, then at least one $R^1$ is other than halogen, —($C_1$-$C_8$)hydrocarbyl, —$NR^w_2$, —$NO_2$, and —$OR^w$.

According to some embodiments of compounds according to the invention, when M is (b), then n is other than 0, and $R^1$ is other than 7-$NR^w_2$ or 7—Cl.

It is to be understood that two —($C_1$-$C_8$)hydrocarbyl $R^1$ substituents on adjacent carbon atoms of a compound of the invention (i.e., at positions 5 and 6, at positions 6 and 7, or at positions 7 and 8) may combine to form an aryl ring. One example of such a compound is [(2-oxobenzo[g]chromen-3-yl)carbonyl]benzo[g]chromen-2-one.

According to some embodiments, $R^y$ is selected from the group consisting of —H, —($C_1$-$C_8$) hydrocarbyl, —($C_1$-$C_8$) hydrocarbyl, substituted phenyl, substituted heterocyclyl($C_1$-$C_3$)alkyl, heteroaryl($C_1$-$C_3$)alkyl, —$C_2$-$C_{10}$)heteroalkyl, —($C_1$-$C_6$)haloalkyl, —CH($R^z$)$NHR^x$, —N($R^w$)$R^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$-$C_3$)alkylene-$OR^x$, —($C_1$-$C_4$)alkylene-$CO_2R^x$, —($C_1$-$C_4$)alkylene-$CO_2$N($R^w$)$R^x$, halo($C_1$-$C_3$)alkyl and —($C_1$-$C_4$)perfluoroalkylene-$CO_2R^x$.

According to other embodiments, $R^y$ is selected from the group consisting of —H, —($C_1$-$C_6$)alkyl, —O($C_1$-$C_6$)alkyl, substituted phenyl, substituted heterocyclyl($C_1$-$C_3$)alkyl, heteroaryl($C_1$-$C_3$)alkyl, —($C_2$-$C_6$)heteroalkyl, —($C_1$-$C_6$)haloalkyl, —CH($R^z$)$NHR^x$, —$NHR^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$-$C_3$)alkylene-$OR^x$, —($C_1$-$C_4$)alkylene-$CO_2R^x$, —($C_1$-$C_4$)alkylene-$CO_2NHR^x$, halo($C_1$-$C_3$)alkyl and —($C_1$-$C_4$)perfluoroalkylene-$CO_2R^x$.

According to still other embodiments, $R^y$ is selected from the group consisting of —H, —($C_1$-$C_6$)alkyl, —O($C_1$-$C_6$) alkyl, substituted phenyl, substituted heterocyclyl($C_1$-$C_3$) alkyl, heteroaryl($C_1$-$C_3$)alkyl, —($C_1$-$C_6$)haloalkyl, —CH($R^z$)$NHR^x$, —$NHR^x$, —($C_1$-$C_3$)alkyleneNH$_2$, —($C_1$-$C_3$)alkyleneN(CH$_3$)$_2$, —($C_1$-$C_3$)alkylene-$OR^x$, —($C_1$-$C_4$)alkylene-$CO_2R^x$, —($C_1$-$C_4$)alkylene-$CO_2NHR^x$ and halo($C_1$-$C_3$)alkyl.

According to some embodiments of compounds according to the invention, the carbon-carbon double bond, which may be a structural feature of M when M is (a) or (c), is in the E-conformation. According to other embodiments of compounds according to the invention, the carbon-carbon double bond, which may be a structural feature of M when M is (a) or (c), is in the Z-conformation.

A. Compounds According to Formula IA

According to a first sub-embodiment of the compounds of the invention, there is provided a compound according to Formula IA:

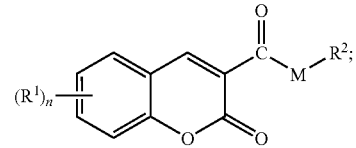

IA wherein $R^1$, $R^2$, $R^w$, $R^x$, $R^y$, $R^z$, $R^3$, A, M and n are as defined herein for compounds of Formula I.

According to a first embodiment of compounds of Formula IA, there is provided a compound wherein M is (a):

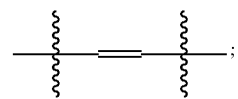

(a)

or a salt of such a compound.

Preferred compounds according to the first embodiment of compounds according to Formula IA include:

3-(E)-(4-methoxystyrylcarbonyl)-6-bromo-2H-chromen-2-one; 3-(E)-(4-chlorostyrylcarbonyl)-6-bromo-2H-chromen-2-one; 3-(E)-(2,4-dichlorostyrylcarbonyl)-6-bromo-2H-chromen-2-one; 3-(E)-(4-methoxystyrylcarbonyl)-6-chloro-2H-chromen-2-one; 3-(E)-(4-chlorostyrylcarbonyl)-6-chloro-2H-chromen-2-one; 3-(E)-(2,4-dichlorostyrylcarbonyl)-6-chloro-2H-chromen-2-one; 3-(E)-(4-methoxystyrylcarbonyl)-5,7-dimethoxy-2H-chromen-2-one; 3-(E)-(4-chlorostyrylcarbonyl)-5,7-dimethoxy-2H-chromen-2-one; 3-(E)-(2,4-dichlorostyrylcarbonyl)-5,7-dimethoxy-2H- chromen-2-one; 3-(E)-(4-methoxystyryl-carbonyl)-7-methoxy-2H-chromen-2-one; 3-(E)-(4-chlorostyrylcarbonyl)-7-methoxy-2H-chromen-2-one; 3-(E)-(2,4-dichlorostyrylcarbonyl)-7-methoxy-2H-chromen-2-one; 3-(Z)-(4-methoxystyrylcarbonyl)-6-bromo-2H-chromen-2-one; 3-(Z)-(4-chlorostyrylcarbonyl)-6-bromo-2H-chromen-2-one; 3-(Z)-(2,4-dichlorostyrylcarbonyl)-6-bromo-2H-chromen-2-one; 3-(4-(4-methoxystyrylcarbonyl)-6-chloro-2H-chromen-2-one; 3-(Z)-(4-chlorostyrylcarbonyl)-6-chloro-2H-chromen-2-one; 3-(Z)-(2,4-dichlorostyrylcarbonyl)-6-chloro-2H-chromen-2-one; 3-(Z)-(4-methoxystyrylcarbonyl)-5,7-dimethoxy-2H-chromen-2-one; 3-(Z)-(4-chlorostyrylcarbonyl)-5,7-dimethoxy-2H-chromen-2-one; 3-(Z)-(2,4-dichlorostyrylcarbonyl)-5,7-dimethoxy-2H-chromen-2-one; 3-(Z)-(4-methoxystyryl-carbonyl)-7-methoxy-2H-chromen-2-one; 3-(2)-(4-chlorostyrylcarbonyl)-7-methoxy-2H-chromen-2-one; 3-(Z)-(2,4-dichlorostyrycarbonyl)-7-methoxy-2H-chromen-2-one; mixtures thereof; and salts thereof.

According to a second embodiment of compounds of Formula IA, there is provided a compound wherein M is (b):

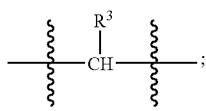
(b)

or a salt of such a compound.

Preferred compounds according to the second embodiment of compounds according to Formula IA include:
3-(4-chlorobenzylcarbonyl)-2H-chromen-2-one; 3-(2,4-dichlorobenzylcarbonyl)-2H-chromen-2-one; 3-(4-methoxy-3-nitrobenzylcarbonyl)-5,7-dimethoxy-2H-chromen-2-one; 3-(4-methoxy-3-nitrobenzylcarbonyl)-7-methoxy-2H-chromen-2-one; 3-(4-methoxy-3-nitrobenzylcarbonyl)-7-hydroxy-2H-chromen-2-one; 3-(4-chloro-3-nitrobenzylcarbonyl)-6-chloro-2H-chromen-2-one; 3-(4-chloro-3-aminobenzylcarbonyl)-6-chloro-2H-chromen-2-one; mixtures thereof; and salts thereof.

Additional preferred compounds according to the second embodiment of compounds according to Formula IA include: 3-(4-methoxybenzylcarbonyl)-2H-chromen-2-one; 3-(4-methoxybenzylcarbonyl)-5,7-dimethoxy-2H-chromen-2-one; 3-(4-methoxybenzylcarbonyl)-6,8-dinitro-2H-chromen-2-one; 3-(4-methoxybenzylcarbonyl)-6-bromo-2H-chromen-2-one; 3-(4-methoxybenzylcarbonyl)-6-chloro-2H-chromen-2-one; 3-(4-methoxybenzylcarbonyl)-7-methoxy-2H-chromen-2-one; 3-(4-methoxybenzylcarbonyl)-7-hydroxy-2H-chromen-2-one; mixtures thereof; and salts thereof.

According to a third embodiment of compounds of Formula IA, there is provided a compound wherein:
M is a single bond;
each $R^1$ is independently selected from the group consisting of, each $R^1$ is independently selected from the group consisting of halogen, —($C_1$-$C_8$)hydrocarbyl, —C(=O)$R^y$, —N($R^w$)C(=O)$R^y$, —N($R^w$)CH($R^z$)C(=O)$R^y$, —N($R^w$)SO$_2R^y$, —N($R^w$)($C_1$-$C_4$)alkylene-CO$_2R^w$, —NO$_2$, —CN, —O$R^w$, —OC(=O)$R^y$, —OCH($R^z$)C(=O)$R^y$, —OSO$_2R^y$—O($C_1$-$C_4$)alkylene-CO$_2R^w$, —OP(=O)(O$R^w$)$_2$, —O($C_2$-$C_6$)alkylene-N(CH$_3$)$_2$, —O($C_1$-$C_6$)haloalkyl, —P(=O)(O$R^w$)$_2$, —SO$_2$N($R^w$)$R^x$, —NHC(=NH)NH$R^x$, —($C_1$-$C_6$)haloalkyl and heteroalkyl; and $R^2$ is:

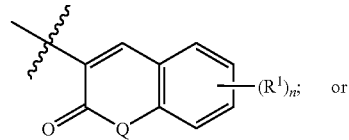
or a salt of such a compound.

According to some preferred embodiments of compounds according to the third embodiment of compounds according to Formula IA, $R^2$ is:

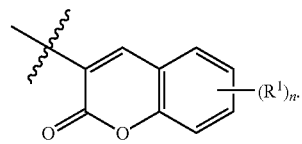

Preferred compounds according to the third embodiment of compounds according to Formula IA include: 8-ethoxy-3-[(8-ethoxy-2-oxochromen-3-yl)carbonyl]chromen-2-one; [(2-oxochromen-3-yl)carbonyl]quinolin-2-one; [(2-oxochromen-3-yl) carbonyl]thio-chromen-2-one; 6-fluoro-3-[(6-fluoro-2-oxochromen-3-yl)carbonyl]chromen-2-one; 6-iodo-3-[(6-iodo-2-oxochromen-3-yl)carbonyl]chromen-2-one; 8-methoxy-3-[(8-methoxy-6-nitro-2-oxochromen-3-yl)carbonyl]-6-nitrochromen-2-one; 6,8-dichloro-3-[(6,8-dichloro-2-oxochromen-3-yl)carbonyl]chromen-2-one; 6,8-dibromo-3-[(6,8-dibromo-2-oxo-chromen-3-yl)carbonyl]chromen-2-one; 6,8-difluoro-3-[(6,8-difluoro-2-oxochromen-3-yl)-carbonyl]chromen-2-one; 5-bromo-8-methoxy-3-[(5-bromo-8-methoxy-2-oxochromen-3-yl)carbonyl]chromen-2-one; 6-bromo-8-methoxy-3-[(6-bromo-8-methoxy-2-oxochromen-3-yl)carbonyl]chromen-2-one; 8-hydroxy-3-[(8-hydroxy-2-oxochromen-3-yl)-carbonyl]chromen-2-one; 6-hydroxy-3-[(6-hydroxy-2-oxochromen-3-yl)carbonyl]-chromen-2-one; 6-chloro-8-bromo-3-[(6-chloro-8-bromo-2-oxochromen-3-yl)carbonyl]-chromen-2-one; [(2-oxobenzo[g]chromen-3-yl)carbonyl]benzo[g]chromen-2-one; 6-methyl-3-[(6-methyl-2-oxochromen-3-yl)carbonyl]chromen-2-one; 6-trifluoromethoxy-3-[(6-trifluoromethoxy-2-oxochromen-3-yl)carbonyl]chromen-2-one; 8-nitro-3-[(8-nitro-2-oxochromen-3-yl)carbonyl]chromen-2-one; 6-bromo-8-nitro-3-[(6-bromo-8-nitro-2-oxo-chromen-3-yl)carbonyl]chromen-2-one; 8-fluoro-3-[(8-fluoro-2-oxochromen-3-yl)carbonyl]chromen-2-one; 6-nitro-8-bromo-3-[(6-nitro-8-bromo-2-oxochromen-3-yl)carbonyl]chromen-2-one; 6,8-dinitro-3-[(6,8-dinitro-2-oxochromen-3-yl)carbonyl]chromen-2-one; mixtures thereof; and salts thereof.

According to a fourth embodiment of compounds of Formula IA, there is provided a compound wherein M is (c):

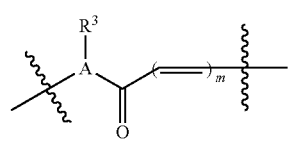
(c)

or a salt of such a compound.

According to some sub-embodiments of the fourth embodiment of compounds according to Formula IA, m is 0 and $R^2$ is:

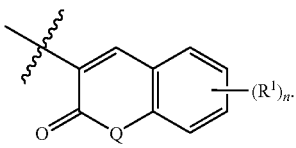

According to some preferred embodiments of compounds according to the fourth embodiment of compounds according to Formula IA, R² is:

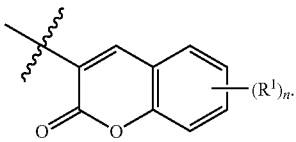

According to other sub-embodiments of the fourth embodiment of compounds according to Formula IA, m is 1, and R² is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl.

Preferred compounds according to the fourth embodiment of compounds according to Formula IA include: 6-chloro-3-({[(6-chloro-2-oxochromen-3-yl)carbonyl]methyl}-carbonyl)chromen-2-one; 6-bromo-3-({[(6-bromo-2-oxo-chromen-3-yl)carbonyl]methyl}-carbonyl)chromen-2-one; 6-iodo-3-({[(6-iodo-2-oxochromen-3-yl)carbonyl]methyl}-carbonyl)chromen-2-one; 8-ethoxy-3-({[(8-ethoxy-2-oxo-chromen-3-yl)carbonyl]methyl}-carbonyl)chromen-2-one; 3-({[(5,7-dimethoxy-2-oxochromen-3-yl)carbonyl]methyl}carbonyl)-5,7-dimethoxychromen-2-one; 7-methoxy-3-({[(7-methoxy-2-oxochromen-3-yl)carbonyl]methyl}carbonyl)-chromen-2-one; 5-methoxy-3-({[(5-methoxy-2-oxo-chromen-3-yl)carbonyl]methyl}-carbonyl)-chromen-2-one; 7-hydroxy-3-({[(7-hydroxy-2-oxochromen-3-yl)carbonyl]-methyl}carbonyl)-chromen-2-one; 3-({[(6,8-dinitro-2-oxo-chromen-3-yl)carbonyl]methyl}carbonyl)-6,8-dinitro-chromen-2-one; 6-chloro-3-(N-[(6-chloro-2-oxochromen-3-yl)carbonyl]carbonyl)chromen-2-one; 6-bromo-3-(N-[(6-bromo-2-oxochromen-3-yl)carbonyl]carbonyl)chromen-2-one; 6-iodo-3-(N-[(6-iodo-2-oxo-chromen-3-yl)carbonyl]carbonyl)chromen-2-one; 8-ethoxy-3-(N-[(8-ethoxy-2-oxo-chromen-3-yl)carbonyl]carbonyl)chromen-2-one; 7-methoxy-3-(N-[(7-methoxy-2-oxo-chromen-3-yl)carbonyl]carbonyl)chromen-2-one; 5-methoxy-3-(N-[(5-methoxy-2-oxo-chromen-3-yl)carbonyl]carbonyl)chromen-2-one; 7-hydroxy-3-(N-[(7-hydroxy-2-oxo-chromen-3-yl)carbonyl]carbonyl)chromen-2-one; 6,8-dinitro-3-(N-[(6,8-dinitro-2-oxo-chromen-3-yl)carbonyl]carbonyl)chromen-2-one; 3-(E)-((4-methoxystyrylcarbonyl)-methylcarbonyl)-7-chloro-2H-chromen-2-one; 3-(E)-((4-methoxystyrylcarbonyl)methyl-carbonyl)-6-chloro-2H-chromen-2-one; 3-(E)-((4-methoxystyrylcarbonyl)methylcarbonyl)-6-bromo-2H-chromen-2-one; 3-(E)-((4-methoxystyrylcarbonyl)methylcarbonyl)-7-iodo-2H-chromen-2-one; 3-(E)-((4-methoxystyrylcarbonyl)methylcarbonyl)-8-ethoxy-2H-chromen-2-one; 3-(E)-((4-methoxystyrylcarbonyl)methylcarbonyl)-7-methoxy-2H-chromen-2-one; 3-(E)-((4-methoxystyrylcarbonyl)methylcarbonyl)-5-methoxy-2H-chromen-2-one; 3-(E)-((4-methoxystyrylcarbonyl)methylcarbonyl)-5,7-dimethoxy-2H-chromen-2-one; 3-(Z)-((4-methoxystyrylcarbonyl)methylcarbonyl)-7-chloro-2H-chromen-2-one; 3-(Z)-((4-methoxy-styrylcarbonyl)methylcarbonyl)-6-chloro-2H-chromen-2-one; 3-(Z)-((4-methoxystyryl-carbonyl)methylcarbonyl)-6-bromo-2H-chromen-2-one; 3-(Z)-((4-methoxystyrylcarbonyl)-methylcarbonyl)-7-iodo-2H-chromen-2-one; 3-(Z)-((4-methoxy-styrylcarbonyl)methylcarbonyl)-8-ethoxy-2H-chromen-2-one; 3-(Z)-((4-methoxystyryl-carbonyl)methylcarbonyl)-7-methoxy-2H-chromen-2-one; 3-(Z)-((4-methoxystyryl-carbonyl)methylcarbonyl)-5-methoxy-2H-chromen-2-one; 3-(Z)-((4-methoxystyrylcarbonyl)methylcarbonyl)-5,7-dimethoxy-2H-chromen-2-one; 3-((E)-4-(4-methoxyphenyl)-2-oxobut-3-enylcarbonyl)-7-chloro-2H-chromen-2-one, 3-((E)-4-(4-methoxyphenyl)-2-oxobut-3-enylcarbonyl)-6-chloro-2H-chromen-2-one; 3-((E)-4-(4-methoxyphenyl)-2-oxobut-3-enylcarbonyl)-6-bromo-2H-chromen-2-one; 3-((E)-4-(4-methoxyphenyl)-2-oxobut-3-enylcarbonyl)-6-iodo-2H-chromen-2-one; 3-((E)-4-(4-methoxyphenyl)-2-oxobut-3-enyl-carbonyl)-8-ethoxy-2H-chromen-2-one; 3-((E)-4-(4-methoxyphenyl)-2-oxobut-3-enyl-carbonyl)-7-methoxy-2H-chromen-2-one; 3-((E)-4-(4-methoxyphenyl)-2-oxobut-3-enyl-carbonyl)-5-methoxy-2H-chromen-2-one; 3-((E)-4-(4-methoxyphenyl)-2-oxobut-3-enyl carbonyl)-5,7-diethoxy-2H-chromen-2-one; 3-((Z)-4-(4-methoxyphenyl)-2-oxobut-3-enylcarbonyl)-7-chloro-2H-chromen-2-one, 3-((Z)-4-(4-methoxyphenyl)-2-oxobut-3-enyl-carbonyl)-6-chloro-2H-chromen-2-one; 3-((Z)-4-(4-methoxyphenyl)-2-oxobut-3-enyl-carbonyl)-6-bromo-2H-chromen-2-one; 3-((Z)-4-(4-methoxyphenyl)-2-oxobut-3-enyl-carbonyl)-6-iodo-2H-chromen-2-one; 3-((Z)-4-(4-methoxyphenyl)-2-oxobut-3-enylcarbonyl)-8-ethoxy-2H-chromen-2-one; 3-((Z)-4-(4-methoxyphenyl)-2-oxobut-3-enylcarbonyl)-7-methoxy-2H-chromen-2-one; 3-((Z)-4-(4-methoxyphenyl)-2-oxobut-3-enylcarbonyl)-5-methoxy-2H-chromen-2-one; 3-((Z)-4-(4-methoxyphenyl)-2-oxobut-3-enylcarbonyl)-5,7-dimethoxy-2H-chromen-2-one; 8-ethoxy-N-((E)-3-(4-methoxyphenyl)acryloyl)-2-oxo-2H-chromene-3-carboxamide; 8-ethoxy-N-((E)-3-(4-methoxyphenyl)acryloyl)-2-oxo-2H-chromene-3-carboxamide; 6-chloro-N-((E)-3-(4-methoxyphenyl)acryloyl)-2-oxo-2H-chromene-3-carboxamide; 6-bromo-N-((E)-3-(4-methoxyphenyl)acryloyl)-2-oxo-2H-chromene-3-carboxamide; 7-iodo-N-((E)-3-(4-methoxyphenyl)acryloyl)-2-oxo-2H-chromene-3-carboxamide; 5-m oxy-N-((E)-3-(4-methoxyphenyl)acryloyl)-2-oxo-2H-chromene-3-carboxamide; 5-methoxy-N-((E)-3-(4-methoxyphenyl)acryloyl)-2-oxo-chromene-3-carboxamide; 5,7-dimethoxy-N-((E)-3-(4-methoxyphenyl)acryloyl)-2-oxo-2H-chromene-3-carboxamide; 8-ethoxy-N-((Z)-3-(4-methoxyphenyl)acryloyl)-2-oxo-2H-chromene-3-carboxamide; 7-chloro-N-((Z)-3-(4-methoxyphenyl)acryloyl)-2-oxo-2H-chromene-3-carboxamide; 7-chloro-N-((Z)-3-(4-methoxyphenyl)acryloyl)-2-oxo-2H-chromene-3-carboxamide; 6-bromo-1-((Z)-3-(4-methoxyphenyl)acryloyl)-2-oxo-2H-chromene-3-carboxamide; 7-iodo-N-((Z)-3-(4-methoxyphenyl)acryloyl)-2-oxo-2H-chromene-3-carboxamide; 5-m oxy-N-((Z)-3-(4-methoxyphenyl)acryloyl)-2-oxo-2H-chromene-3-carboxamide; 5-methoxy-N-((Z)-3-(4-methoxyphenyl)acryloyl)-2-oxo-2H-chromene-3-carboxamide; 5,7-dimethoxy-N-((Z)-3-(4-methoxyphenyl)acryloyl)-2-oxo-2H-chromene-3-carboxamide; mixtures thereof; and salts thereof B. Compounds According to Formula IB According to a second sub-embodiment of the compounds of the invention, there is provided a compound according to Formula IB:

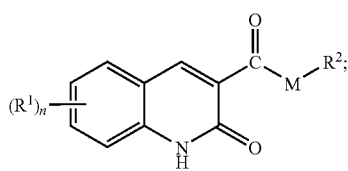

wherein $R^1$, $R^2$, $R^w$, $R^x$, $R^y$, $R^z$, $R^3$, A, M and n are as defined herein for compounds of Formula I.

According to a first embodiment of compounds of Formula IB, there is provided a compound wherein M is (a):

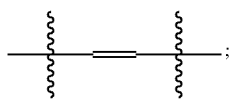

or a salt of such a compound.

Preferred compounds according to the first embodiment of compounds according to Formula IB include: 7-chloro-3-(E)-(4-methoxystyrylcarbonyl)quinolin-2(1H-one; 3-(E)-(4-methoxystyrylcarbonyl)quinolin-2(1H)-one; 5,7-dibromo-3-(E)-(4-methoxystyryl-carbonyl)quinolin-2(1H)-one; 7-chloro-3-(E)-(4-chlorostyrylcarbonyl)quinolin-2(1H)-one; 3-(E)-(4-chlorostyrylcarbonyl)quinolin-2(1H)-one; 5,7-dibromo-3-(E)-(4-chlorostyryl-carbonyl)quinolin-2(1H)-one; 7-chloro-3-(E)-(2,4-dichlorostyrylcarbonyl)quinolin-2(1H-one; 3-(E)-(2,4-dichlorostyrylcarbonyl)quinolin-2(1H)-one; 5,7-dibromo-3-(E)-(2,4-dichlorostyrylcarbonyl)quinolin-2(1H)-one; 7-chloro-3-(Z)-(4-methoxystyrylcarbonyl)-quinolin-2(1H)-one; 3-(Z)-(4-methoxystyrylcarbonyl)quinolin-2(1H)-one; 5,7-dibromo-3-(Z)-(4-methoxystyrylcarbonyl)quinolin-2(1H)-one; 7-chloro-3-(Z)-(4-chlorostyryl-carbonyl)quinolin-2(1H)-one; 3-(Z)-(4-chlorostyrylcarbonyl)quinolin-2(1H)-one; 5,7-dibromo-3-(Z)-(4-chlorostyrylcarbonyl)quinolin-2(1H)-one; 7-chloro-3-(Z)-(2,4-dichloro-5,7-dibromo-3-(Z)-(2,4-dichlorostyrylcarbonyl)quinolin-2(1H)-one mixtures thereof; and salts thereof.

According to a second embodiment of compounds of Formula IB, there is provided a compound wherein M is (b):

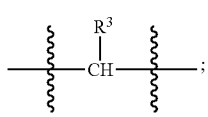

or a salt of such a compound.

Preferred compounds according to the second embodiment of compounds according to Formula IB include:

3-(4-methoxybenzylcarbonyl)-7-chloroquinolin-2(1H)-one; 3-(4-methoxybenzyl-carbonyl)quinolin-2(1H)-one; 3-(4-methoxybenzylcarbonyl)-5,7-dibromoquinolin-2(1H)-one; 3-(4-chlorobenzylcarbonyl)-7-chloroquinolin-2(1H)-one; 3-(4-chlorobenzyl-carbon-yl)quinolin-2(1H)-one; 3-(4-chlorobenzylcarbonyl)-5,7-dibromoquinolin-2(1H)-one; 3-(2,4-dichlorobenzylcarbonyl)-7-chloroquinolin-2(1H)-one; 3-(2,4-dichlorobenzyl-carbon-yl)quinolin-2(1H)-one; 3-(2,4-dichlorobenzylcarbonyl)-5,7-dibromoquinolin-2(1H)-one; 3-(4-methoxy-3-nitrobenzylcarbonyl)-7-chloroquinolin-2(1H)-one; 3-(4-methoxy-3-nitro-benzylcarbonyl)quinolin-2(1H)-one; 3-(4-methoxy-3-nitrobenzylcarbonyl)-5,7-dibromo-quinolin-2(1H)-one; 3-(4-chloro-3-nitrobenzylcarbonyl)-7-chloroquinolin-2(1H)-one; 3-(4-chloro-3-nitrobenzylcarbonyl)quinolin-2(1H)-one; 3-(4-chloro-3-nitrobenzylcarbonyl)-5,7-dibromoquinolin-2(1H)-one; 3-(4-chloro-3-aminobenzyl-carbonyl)-7-chloroquinolin-2(1H)-one; 3-(4-chloro-3-aminobenzylcarbonyl)quinolin-2(1H)-one; 3-(4-chloro-3-amino-benzylcarbonyl)-5,7-dibromoquinolin-2(1H)-one; mixtures thereof; and salts thereof.

According to a third embodiment of compounds of Formula IB, there is provided a compound wherein M is a single bond;

each $R^1$ is independently selected from the group consisting of halogen, —($C_1$-$C_8$)hydrocarbyl, —C(=O)$R^y$, —N($R^w$)C(=O)$R^y$, —N($R^w$)CH($R^z$)C(=O)$R^y$, —N($R^w$)$SO_2R^y$, —N($R^w$)($C_1$-$C_4$)alkylene-$CO_2R^w$, —$NO_2$, —CN, —$OR^w$, —OC(=O)$R^y$, —OCH($R^z$)C(=O)$R^y$, —$OSO_2R^y$—O($C_1$-$C_4$)alkylene-$CO_2R^w$, —OP(=O)($OR^w$)$_2$, —O($C_2$-$C_6$)alkylene-N($CH_3$)$_2$, —O($C_1$-$C_6$)haloalkyl, —P(=O)($OR^w$)$_2$, —$SO_2$N($R^w$)$R^x$, —NHC(=NH)$NHR^x$, —($C_1$-$C_6$)haloalkyl and heteroalkyl; and $R^2$ is:

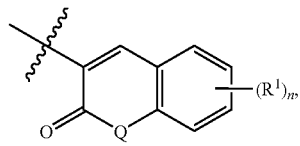

or a salt of such a compound.

According to some preferred embodiments of compounds according to the third embodiment of compounds according to Formula IB, $R^2$ is:

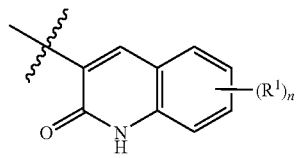

Preferred compounds according to the third embodiment of compounds according to Formula IB include: 7-chloro-3-[(7-chloro-2-quinolon-3-yl)carbonyl]-2-quinolone; 5,7-dibromo-3-[(5,7-dibromo-2-quinolon-3-yl)carbonyl]-2-quinolone; 3-[(2-quinolon-3-yl)-carbonyl]-2-quinolone; [(2-quinolon-3-yl)carbonyl]thiochromen-2-one; 6-bromo-3-[(6-bromo-2-quinolon-3-yl)carbonyl]-chromen-2-one; 7-methoxy-3-[(7-methoxy-2-quinolon-3-yl)carbonyl]-2-quinolone; 8-ethoxy-3-[(8-ethoxy-2-quinolon-3-yl)carbonyl]-2-quinolone; 6-chloro-3-[(6-chloro-2-quinolon-3-yl)carbonyl]-2-quinolone; 6-fluoro-3-[(6-fluoro-2-quinolon-3-yl)carbonyl]-2-quinolone; 6-iodo-3-[(6-iodo-2-quinolon-3-yl)carbonyl]-2-quinolone; 6-nitro-3-[(6-nitro-2-quinolon-3-yl)carbonyl]-2-quinolone; 8-methoxy-3-[(8-methoxy-6-nitro-2-quinolon-3-yl)carbonyl]-6-nitro-2-quinolone; 7-hydroxy-3-[(7-hydroxy-2-quinolon-3-yl)carbonyl]-2-quinolone; 6,8-dichloro-3-[(6,8-dichloro-2-quinolon-3-yl)carbonyl]-2-quinolone; 6,8-dibromo-3-[(6,8-dibromo-2-quinolon-3-yl)-carbonyl]-2-quinolone; 6,8-difluoro-3-[(6,8-difluoro-2-quinolon-3-yl)carbonyl]-2-quinolone; 5-bromo-8-methoxy-3-[(5-bromo-8-methoxy-2-quinolon-3-yl)carbonyl]-2-quinolone; 6-bromo-8-methoxy-3-[(6-bromo-8- methoxy-2-quinolon-3-yl)carbonyl]-2-quinolone; 8-hydroxy-3-[(8-hydroxy-2-quinolon-3-yl)carbonyl]-2-quinolone; 6-hydroxy-3-[(6-hydroxy-2-quinolon-3-yl)carbonyl]-2-quinolone; —6-chloro-8-bromo-3-[(6-chloro-8-bromo-2-quinolon-3-yl)carbonyl]-2-quinolone; [(2-oxobenzo[g]chromen-2-yl)carbonyl]-benzo[g]-2-quinolone; 5-methoxy-3-[(5-methoxy-2-quinolon-3-yl)carbonyl]-2-quinolone; 6-methyl-3-[(6-methyl-2-quinolon-3-yl)carbonyl]-2-quinolone; 6-trifluoromethoxy-3-[(6-trifluoromethoxy-2-quinolon-3-yl)carbonyl]-2-quinolone; 8-nitro-3-[(8-nitro-2-quinolon-3-yl)carbonyl]-2-quinolone; 6-bromo-8-nitro-3-[(6-bromo-8-nitro-2-quinolon-3-yl)carbonyl]-2-quinolone; 8-fluoro-3-[(8-fluoro-2-quinolon-3-yl)carbonyl]-2-quinolone; 6-nitro-8-bromo-3-[(6-nitro-8-bromo-2-quinolon-3-yl)carbonyl]-2-quinolone; 6,8-dinitro-3-[(6,8-dinitro-2-quinolon-3-yl)carbonyl]-chromen-2-one; mixtures thereof; and salts thereof.

According to a fourth embodiment of compounds of Formula IB, there is provided a compound wherein M is (c):

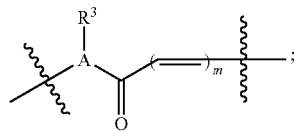

or a salt of such a compound.

According to some sub-embodiments of the fourth embodiment of compounds according to Formula IB, m is 0 and $R^2$ is:

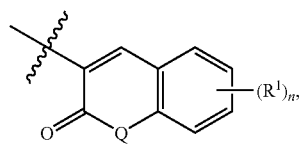

or a salt of such a compound.

According to some preferred sub-embodiments of compounds according to the fourth embodiment of compounds according to Formula IB, $R^2$ is:

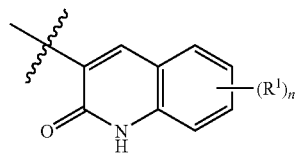

According to other sub-embodiments of the fourth embodiment of compounds according to Formula IB, m is 1, and $R^2$ is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl.

Preferred compounds according to the fourth embodiment of compounds according to Formula IB include:

7-chloro-3-({[(7-chloro-2-quinolone-3-yl)carbonyl]methyl}carbonyl)-2-quinolone; 3-({[(2-quinolone-3-yl)carbonyl]methyl}carbonyl)-2-quinolone; 5,7-dibromo-3-({[(5,7-dibromo-2-quinolone-3-yl)carbonyl]methyl}carbonyl)-2-quinolone; 3-((4-methoxystyryl-carbonyl)methylcarbonyl)-7-chloroquinolin-2(1H)-one; 3-((4-methoxystyrylcarbonyl)methylcarbonyl)quinolin-2(1H)-one; 3-((4-methoxystyrylcarbonyl)methylcarbonyl)-5,7-dibromoquinolin-2(1H)-one; 3-((E)-4-(4-methoxyphenyl)-2-oxobut-3-enylcarbonyl)-7-chloroquinolin-2(1H)-one; 3-((E)-4-(4-chlorophenyl)-2-oxobut-3-enylcarbonyl)-7-chloro-quinolin-2(1H)-one; 3-((E)-4-(2,4-dichlorophenyl)-2-oxobut-3-enylcarbonyl)-7-chloro-quinolin-2(1H)-one; 3-((E)-4-(4-chloro-3-nitrophenyl)-2-oxobut-3-enylcarbonyl)-7-chloro-quinolin-2(1H)-one; 3-((E)-4-(4-chloro-3-aminophenyl)-2-oxobut-3-enylcarbonyl)-7-chloroquinolin-2(1H)-one; 3-((E)-4-(4-methoxyphenyl)-2-oxobut-3-enylcarbonyl)-quinolin-2(1H)-one; 3-((E)-4-(4-chlorophenyl)-2-oxobut-3-enylcarbonyl)quinolin-2(1H)-one; 3-((Z)-4-(4-methoxyphenyl)-2-oxobut-3-enylcarbonyl)-7-chloroquinolin-2(1H)-one; 3-((Z)-4-(4-chlorophenyl)-2-oxobut-3-enylcarbonyl)-7-chloroquinolin-2(1H)-one; 3-((Z)-4-(2,4-dichlorophenyl)-2-oxobut-3-enylcarbonyl)-7-chloroquinolin-2(1H)-one; 3-((Z)-4-(4-chloro-3-nitrophenyl)-2-oxobut-3-enylcarbonyl)-7-chloroquinolin-2(1H)-one; 3-((Z)-4-(4-chloro-3-aminophenyl)-2-oxobut-3-enylcarbonyl)-7-chloroquinolin-2(1H)-one; 3-((Z)-4-(4-methoxyphenyl)-2-oxobut-3-enylcarbonyl)quinolin-2(1H)-one; 3-((Z)-4-(4-chlorophenyl)-2-oxobut-3-enylcarbonyl)quinolin-2(1H)-one; mixtures thereof; and salts thereof.

C. Compounds According to Formula IC

According to a third sub-embodiment of the compounds of the invention, there is provided a compound according to Formula IC:

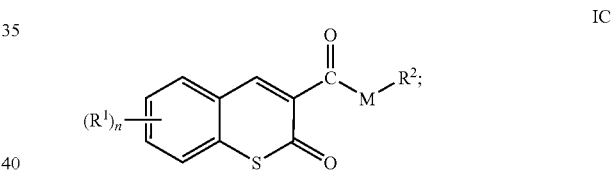

wherein $R^1$, $R^2$, $R^w$, $R^x$, $R^y$, $R^z$, $R^3$, A, M and n are as defined herein for compounds of Formula I.

According to a first embodiment of compounds of Formula IC, there is provided a compound wherein M is (a):

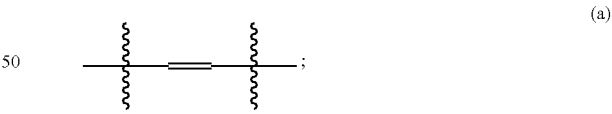

or a salt of such a compound.

Preferred compounds according to the first embodiment of compounds according to Formula IC include: 3-(E)-(4-methoxystyrylcarbonyl)-6-bromo-2H-thiochromen-2-one; 3-(E)-(4-chlorostyrylcarbonyl)-6-bromo-2H-thiochromen-2-one; 3-(E)-(2,4-dichloro-styrylcarbonyl)-6-bromo-2H-thiochromen-2-one; 3-(E)-(4-methoxystyrylcarbonyl)-6-chloro-2H-thiochromen-2-one; 3-(E)-(4-chlorostyrylcarbonyl)-6-chloro-2H-thiochromen-2-one; 3-(E)-(2,4-dichlorostyrylcarbonyl)-6-chloro-2H-thiochromen-2-one; 3-(E)-(4-methoxystyryl-carbonyl)-5,7-dimethoxy-2H-thiochromen-2-one; 3-(E)-(4-chlorostyryl-carbonyl)-5,7-dimethoxy-2H-thiochromen-2-one; 3-(E)-(2,4-dichlorostyrylcarbonyl)-5,7-dimethoxy-2H-thiochromen-2-one;

3-(E)-(4-methoxystyrylcarbonyl)-7-methoxy-2H-thiochromen-2-one; 3-(E)-(4-chlorostyrylcarbonyl)-7-methoxy-2H-thiochromen-2-one; 3-(E)-(2,4-dichloro-styrylcarbonyl)-7-methoxy-2H-thiochromen-2-one; 3-(Z)-(4-methoxystyryl-carbonyl)-6-bromo-2H-thiochromen-2-one; 3-(Z)-(4-chlorostyrylcarbonyl)-6-bromo-2H-thiochromen-2-one; 3-(Z)-(2,4-dichlorostyrylcarbonyl)-6-bromo-2H-thiochromen-2-one; 3-(Z)-(4-methoxystyrylcarbonyl)-6-chloro-2H-thiochromen-2-one; 3-(Z)-(4-chlorostyrylcarbonyl)-6-chloro-2H-thiochromen-2-one; 3-(Z)-(2,4-dichlorostyrylcarbonyl)-6-chloro-2H-thiochromen-2-one; 3-(Z)-(4-methoxystyrylcarbonyl)-5,7-dimethoxy-2H-thiochromen-2-one; 3-(Z)-(4-chlorostyrylcarbonyl)-5,7-dimethoxy-2H-thiochromen-2-one; 3-(Z)-(2,4-dichlorostyrylcarbonyl)-5,7-dimethoxy-2H-thiochromen-2-one; 3-(Z)-(4-methoxystyryl-carbonyl)-7-methoxy-2H-thiochromen-2-one; 3-(Z)-(4-chlorostyrylcarbonyl)-7-methoxy-2H-thiochromen-2-one; 3-(Z)-(2,4-dichlorostyrylcarbonyl)-7-methoxy-2H-thiochromen-2-one; mixtures thereof; and salts thereof.

According to a second embodiment of compounds of Formula IC, there is provided a compound wherein M is (b):

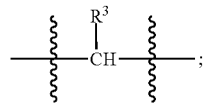
(b)

or a salt of such a compound.

Preferred compounds according to the second embodiment of compounds according to Formula IC include:
3-(4-methoxybenzylcarbonyl)-2H-thiochromen-2-one; 3-(4-methoxybenzyl-carbonyl)-5,7-dimethoxy-2H-thiochromen-2-one; 3-(4-methoxybenzylcarbonyl)-6,8-dinitro-2H-thiochromen-2-one; 3-(4-methoxybenzylcarbonyl)-6-bromo-2H-thiochromen-2-one; 3-(4-methoxybenzylcarbonyl)-6-chloro-2H-thiochromen-2-one; 3-(4-methoxy-benzylcarbonyl)-7-methoxy-2H-thiochromen-2-one; 3-(4-methoxybenzyl-carbonyl)-7-hydroxy-2H-thiochromen-2-one; 3-(4-methoxybenzylcarbonyl)-7-chloro-2H-thiochromen-2-one; 3-(4-methoxybenzylcarbonyl)-5,7-dibromo-2H-thiochromen-2-one; 3-(4-chlorobenzylcarbonyl)-2H-thiochromen-2-one; 3-(4-chlorobenzylcabonyl)-7-chloro-2H-thiochromen-2-one; 3-(4-chlorobenzylcarbonyl)-5,7-dibromo-2H-thiochromen-2-one; 3-(2,4-dichlorobenzylcarbonyl)-2H-thiochromen-2-one; 3-(2,4-dichlorobenzylcarbonyl)-7-chloro-2H-thiochromen-2-one; 3-(2,4-dichlorobenzylcarbonyl)-5,7-dibromo-2H-thio-chromen-2-one; 3-(4-methoxy-3-nitrobenzylcarbonyl)-5,7-dimethoxy-2H-thiochromen-2-one; 3-(4-methoxy-3-nitrobenzylcarbonyl)-7-methoxy-2H-thiochromen-2-one; 3-(4-methoxy-3-nitrobenzylcarbonyl)-7-hydroxy-2H-thiochromen-2-one; 3-(4-methoxy-3-nitrobenzylcarbonyl)-7-chloro-2H-thiochromen-2-one; 3-(4-methoxy-3-nitrobenzylcarbonyl)-2H-thiochromen-2-one; 3-(4-methoxy-3-nitrobenzylcarbonyl)-5,7-dibromo-2H-thio-chromen-2-one; 3-(4-chloro-3-nitrobenzylcarbonyl)-6-chloro-2H-thiochromen-2-one; 3-(4-chloro-3-nitrobenzyl-carbonyl)-7-chloro-2H-thiochromen-2-one; 3-(4-chloro-3-nitro-benzylcarbonyl)-2H-thiochromen-2-one; 3-(4-chloro-3-nitrobenzyl-carbonyl)-5,7-di-bromo-2H-thiochromen-2-one; 3-(4-chloro-3-aminobenzylcarbonyl)-7-chloro-2H-thio-chromen-2-one; 3-(4-chloro-3-aminobenzylcarbonyl)-2H-thiochromen-2-one; 3-(4-chloro-3-aminobenzylcarbonyl)-5,7-dibromo-2H-thiochromen-2-one; 3-(4-chloro-3-aminobenzyl-carbonyl)-6-chloro-2H-thiochromen-2-one; mixtures thereof; and salts thereof.

According to a third embodiment of compounds of Formula IC, there is provided a compound wherein:

M is a single bond;

each $R^1$ is independently selected from the group consisting of halogen, $-(C_1-C_8)$hydrocarbyl, $-C(=O)R^y$, $-N(R^w)C(=O)R^y$, $-N(R^w)CH(R^z)C(=O)R^y$, $-N(R^w)SO_2R^y$, $-N(R^w)(C_1-C_4)$alkylene-$CO_2R^w$, $-NO_2$, $-CN$, $-OR^w$, $-OC(=O)R^y$, $-OCH(R^z)C(=O)R^y$, $-OSO_2R^y$, $-O(C_1-C_4)$alkylene-$CO_2R^w$, $-OP(=O)(OR^w)_2$, $-O(C_2-C_6)$alkylene-$N(CH_3)_2$, $-O(C_1-C_6)$haloalkyl, $-P(=O)(OR^w)_2$, $-SO_2N(R^w)R^x$, $-NHC(=NH)NHR^x$, $-(C_1-C_6)$haloalkyl and heteroalkyl; and $R^2$ is:

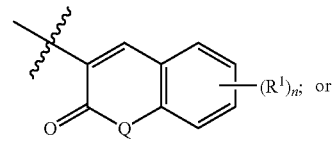

a salt of such a compound.

According to some preferred embodiments of compounds according to the third embodiment of compounds according to Formula IB, $R^2$ is:

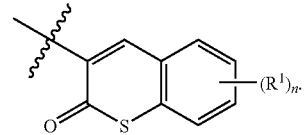

Preferred compounds according to the third embodiment of compounds according to Formula IC include: [(2-oxothiochromen-3-yl)carbonyl]quinolin-2-one; [(2-oxo-thiochromen-3-yl)carbonyl]thiochromen-2-one; 6-bromo-3-[(6-bromo-2-oxothiochromen-3-yl)carbonyl]thiochromen-2-one; 7-methoxy-3-[(7-methoxy-2-oxothiochromen-3-yl)carbonyl]thiochromen-2-one; 8-ethoxy-3-[(8-ethoxy-2-oxothiochromen-3-yl)carbonyl]-thiochromen-2-one; 6-chloro-3-[(6-chloro-2-oxothiochromen-3-yl)carbonyl]thiochromen-2-one; 6-fluoro-3-[(6-fluoro-2-oxothiochromen-3-yl)carbonyl]thiochromen-2-one; 6-iodo-3-[(6-iodo-2-oxothiochromen-3-yl)carbonyl]thiochromen-2-one; 6-nitro-3-[(6-nitro-2-oxo-thiochromen-3-yl)carbonyl]thiochromen-2-one; 8-methoxy-3-[(8-methoxy-6-nitro-2-oxothiochromen-3-yl)carbonyl]-6-nitrothiochromen-2-one; 7-hydroxy-3-[(7-hydroxy-2-oxothiochromen-3-yl)carbonyl]thiochromen-2-one; 6,8-dichloro-3-[(6,8-dichloro-2-oxothiochromen-3-yl)carbonyl]thiochromen-2-one; 6,8-dibromo-3-[(6,8-dibromo-2-oxothiochromen-3-yl)carbonyl]thiochromen-2-one; 6,8-difluoro-3-[(6,8-difluoro-2-oxothiochromen-3-yl)carbonyl]thiochromen-2-one; 5-bromo-8-methoxy-3-[(5-bromo-8-methoxy-2-oxothiochromen-3-yl)carbonyl]thiochromen-2-one; 6-bromo-8-methoxy-3-[(6-bromo-8-methoxy-2-oxothiochromen-3-yl)carbonyl]thiochromen-2-one; 8-hydroxy-3-[(8-hydroxy-2-oxothiochromen-3-yl)carbonyl]thiochromen-2-one; 6-hydroxy-3-[(6-hydroxy-2-oxothiochromen-3-yl)carbonyl]thiochromen-2-one; 6-chloro-8-bromo-3-[(6-chloro-8-bromo-2-oxothiochromen-3-yl)carbonyl]thiochromen-2- one; [(2-oxobenzo[g]thiochromen-3-yl)-carbonyl]benzo[g]
thiochromen-2-one; 5-methoxy-3-[(5-methoxy-2-
oxothiochromen-3-yl)-carbonyl]thiochromen-2-one;
6-methyl-3-[(6-methyl-2-oxothiochromen-3-yl)carbonyl]
thiochromen-2-one; 6-trifluoromethoxy-3-[(6-trifluo-
romethoxy-2-oxothiochromen-3-yl)carbonyl]thiochromen-
2-one; 8-nitro-3-[(8-nitro-2-oxothiochromen-3-yl)carbonyl]
thio-chromen-2-one; 6-bromo-8-nitro-3-[(6-bromo-8-nitro-
2-oxothiochromen-3-yl)carbonyl]-thiochromen-2-one;
8-fluoro-3-[(8-fluoro-2-oxothiochromen-3-yl)carbonyl]
thiochromen-2-one; 6-nitro-8-bromo-3-[(6-nitro-8-bromo-
2-oxothiochromen-3-yl)carbonyl]thio-chromen-2-one; 6,8-
dinitro-3-[(6,8-dinitro-2-oxothiochromen-3-yl)carbonyl]
thiochromen-2-one; mixtures thereof; and salts thereof.

According to a fourth embodiment of compounds of Formula IC, there is provided a compound wherein M is (c):

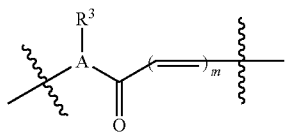

(c)

or a salt of such a compound.

According to some sub-embodiments of the fourth embodiment of compounds according to Formula IC, m is 0 and R² is:

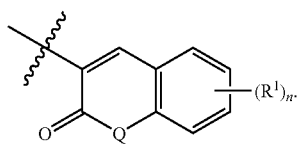

According to some preferred embodiments of compounds according to the fourth embodiment of compounds according to Formula IB, R² is:

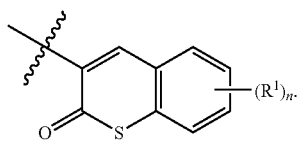

According to other sub-embodiments of the fourth embodiment of compounds according to Formula IC, m is 1, and R² is substituted or unsubstituted aryl, preferably substituted aryl, more preferably substituted phenyl; or substituted or unsubstituted heteroaryl, preferably monocyclic heteroaryl, more preferably 5- or 6-membered ring monocyclic heteroaryl.

Preferred compounds according to the fourth embodiment of compounds according to Formula IC include: 6-chloro-3-({[(6-chloro-2-oxothiochromen-3-yl)carbonyl]-methyl}carbonyl)-thiochromen-2-one; 6-bromo-3-({[(6-bromo-2-oxothiochromen-3-yl)-carbonyl]methyl}-carbonyl)thiochromen-2-one; 6-iodo-3-({[(6-iodo-2-oxothiochromen-3-yl)carbonyl]-methyl}carbonyl) thiochromen-2-one; 8-ethoxy-3-({[(8-ethoxy-2-oxothiochromen-3-yl)carbonyl]methyl}carbonyl) thiochromen-2-one; 3-({[(5,7-dimethoxy-2-oxo-thiochromen-3-yl)carbonyl]methyl}carbonyl)-5,7-dimethoxythiochromen-2-one; 7-methoxy-3-({[(7-methoxy-2-oxothiochromen-3-yl)carbonyl]methyl}carbonyl) thio-chromen-2-one; 5-methoxy-3-({[(5-methoxy-2-oxothiochromen-3-yl)carbonyl]methyl}-carbonyl) thiochromen-2-one; 7-hydroxy-3-({[(7-hydroxy-2-oxothiochromen-3-yl)carbonyl]-methyl}-carbonyl) thiochromen-2-one; 3-({[(6,8-dinitro-2-oxothiochromen-3-yl)-carbonyl]methyl}-carbonyl)-6,8-dinitrothiochromen-2-one; 3-(E)-((4-methoxystyryl-carbonyl)methyl-carbonyl)-7-chloro-2H-thiochromen-2-one; 3-(E)-((4-methoxystyryl-carbonyl)methyl-carbonyl)-6-chloro-2H-thiochromen-2-one; 3-(E)-((4-methoxystyryl-carbonyl)methyl-carbonyl)-6-bromo-2H-thiochromen-2-one; 3-(E)-((4-methoxystyryl-carbonyl)methyl-carbonyl)-7-iodo-2H-thiochromen-2-one; 3-(E)-((4-methoxystyryl-carbonyl)methyl-carbonyl)-8-ethoxy-2H-thiochromen-2-one; 3-(E)-((4-methoxystyryl-carbonyl)methyl-carbonyl)-7-methoxy-2H-thiochromen-2-one; 3-(E)-((4-methoxystyryl-carbonyl)methyl-carbonyl)-5-methoxy-2H-thiochromen-2-one; 3-(E)-((4-methoxystyryl-carbonyl)methyl-carbonyl)-5,7-dimethoxy-2H-thiochromen-2-one; 3-(Z)-((4-methoxy-styrylcarbonyl)methyl-carbonyl)-7-chloro-2H-thiochromen-2-one; 3-(Z)-((4-methoxy-styrylcarbonyl)methyl-carbonyl)-6-chloro-2H-thiochromen-2-one; 3-(Z)-((4-methoxy-styrylcarbonyl)methyl-carbonyl)-6-bromo-2H-thiochromen-2-one; 3-(Z)-((4-methoxy-styrylcarbonyl)-methyl-carbonyl)-7-iodo-2H-thiochromen-2-one; 3-(Z)-((4-methoxystyryl-carbonyl)methyl-carbonyl)-8-ethoxy-2H-thiochromen-2-one; 3-(Z)-((4-methoxystyryl-carbonyl)-methyl-carbonyl)-7-methoxy-2H-thiochromen-2-one; 3-(Z)-((4-methoxystyryl-carbonyl)-methyl-carbonyl)-5-methoxy-2H-thiochromen-2-one; 3-(Z)-((4-methoxy-styrylcarbonyl)-methyl-carbonyl)-5,7-dimethoxy-2H-thiochromen-2-one; 3-((E)-4-(4-methoxyphenyl)-2-oxobut-3-enylcarbonyl)-7-chloro-2H-thio-chromen-2-one, 3-((E)-4-(4-methoxyphenyl)-2-oxobut-3-enylcarbonyl)-6-chloro-2H-thiochromen-2-one; 3-((E)-4-(4-methoxyphenyl)-2-oxobut-3-enylcarbonyl)-6-bromo-2H-thiochromen-2-one; 3-((E)-4-(4-methoxyphenyl)-2-oxobut-3-enylcarbonyl)-6-iodo-2H-thiochromen-2-one; 3-((E)-4-(4-methoxyphenyl)-2-oxobut-3-enylcarbonyl)-8-ethoxy-2H-thiochromen-2-one; 3-((E)-4-(4-methoxyphenyl)-2-oxobut-3-enylcarbonyl)-7-methoxy-2H-thiochromen-2-one; 3-((E)-4-(4-methoxyphenyl)-2-oxobut-3-enylcarbonyl)-5-methoxy-2H-thiochromen-2-one; 3-((E)-4-(4-methoxyphenyl)-2-oxobut-3-enylcarbonyl)-5,7-dimethoxy-2H-thio-chromen-2-one; 3-((Z)-4-(4-methoxy-phenyl)-2-oxobut-3-enylcarbonyl)-7-chloro-2H-thiochromen-2-one, 3-((Z)-4-(4-methoxyphenyl)-2-oxobut-3-enylcarbonyl)-6-chloro-2H-thiochromen-2-one; 3-((Z)-4-(4-methoxyphenyl)-2-oxobut-3-enylcarbonyl)-6-bromo-2H-thiochromen-2-one; 3-((Z)-4-(4-methoxyphenyl)-2-oxobut-3-enylcarbonyl)-6-iodo-2H-thiochromen-2-one; 3-((Z)-4-(4-methoxyphenyl)-2-oxobut-3-enylcarbonyl)-g-ethoxy-2H-thiochromen-2-one; 3-((Z)-4-(4-methoxyphenyl)-2-oxobut-3-enylcarbonyl)-7-methoxy-2H-thiochromen-2-one; 3-((Z)-4-(4-methoxyphenyl)-2-oxobut-3-enylcarbonyl)-5-methoxy-2H-thiochromen-2-one; 3-((Z)-4-(4-methoxyphenyl)-2-oxobut-3-enylcarbonyl)-5,7-dimethoxy-2H-thiochromen-2-one; mixtures thereof, and salts thereof.

The present invention further embraces isolated compounds according to Formula I. The expression "isolated compound" refers to a compound of Formula I, or a mixture of compounds according to Formula I, wherein the isolated compound contains the named compound or mixture of compounds according to Formula I in an amount of at least 10 percent by weight of the total weight. Preferably the isolated compound contains the named compound or mixture of compounds in an amount of at least 50 percent by weight of the total weight; more preferably at least 80 percent by weight of the total weight; and most preferably at least 90 percent or at least 95 percent by weight of the total weight.

II. Intermediates in the Preparation of Formula I Compounds

According to another embodiment of the invention, there are provided synthetic intermediates of Formula II:

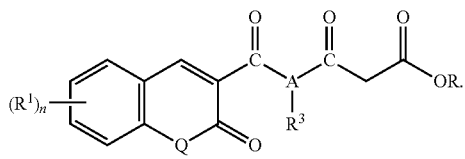

useful in the preparation of compounds according to Formula I wherein M is (c);

wherein $R^1$, $R^3$, A and Q are as defined herein, and R is —H or —($C_1$-$C_7$)hydrocarbyl, preferably benzyl or —($C_1$-$C_6$) alkyl, more preferably —($C_1$-$C_3$) alkyl, most preferably methyl or ethyl.

According to one subembodiment of compounds of Formula II, A is CH. According to another subembodiment of compounds of Formula II, A is N.

Compounds according to Formula II may be prepared, for example, by (a) reacting a compound according to Formula IIA:

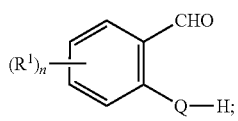

wherein $R^1$, Q and n are as defined herein; with a compound according to Formula IIB:

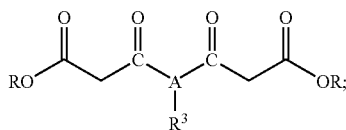

wherein A, R and $R^3$ are as defined herein; and (b) isolating a compound according to Formula II from the reaction products.

Compounds according to Formula IIB, wherein R is —($C_1$-$C_7$)hydrocarbyl, may be prepared, for example by:

(a) reacting a compound according to Formula IIB, wherein R is —H, with a hydrocarbyl alcohol and a catalytic amount of an acid reagent; and (b) isolating a compound according to Formula IIB, wherein R is —($C_1$-$C_7$)hydrocarbyl from the reaction products.

Preferred acid reagents include, for example, sulfuric acid, toluene sulfonic acid and hydrochloric acid.

According to another embodiment of the invention, there are provided synthetic intermediates according to Formula IV:

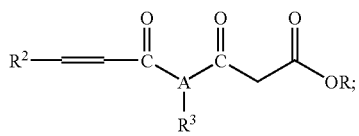

useful in the preparation of compounds according to Formula I wherein M is (c); and A, $R^2$ and $R^3$ are as defined herein, and R is —H or —($C_1$-$C_7$)hydrocarbyl, preferably benzyl or —($C_1$-$C_6$) alkyl, more preferably —($C_1$-$C_3$) alkyl, most preferably methyl or ethyl.

Compounds according to Formula IV may be prepared, for example, by (a) reacting a compound according to Formula IVA:

with a compound according to Formula IIIA:

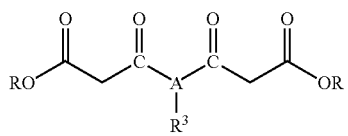

wherein A, $R^2$, $R^3$ and R are as defined herein; and (b) isolating a compound according to Formula IV from the reaction products.

Compounds according to Formula IIB, wherein A is N, may be prepared, for example by:

(a) reacting a compound according to Formula IIIB:

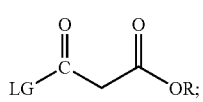

wherein R is —($C_1$-$C_7$)hydrocarbyl and LG is a leaving group, preferably an alkylsulfonate, a haloalkyl sulfonate, an aralkyl sulfonate or a halogen, more preferably a halogen, most preferably Cl;

with a compound of Formula IIIC:

$R^3$—$NH_2$    IIC; and (b) isolating a compound according to Formula IIB from the reaction products.

III. Processes of Preparing Compounds According to Formula I

According to another aspect of the invention, processes for preparing compounds according to Formula I are provided.

According to one embodiment of the invention, a compound according to Formula I:

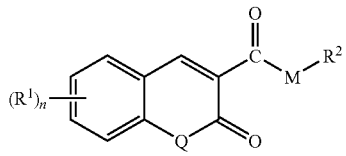

wherein M, $R^1$, $R^2$, Q and n are as defined herein may be prepared by:

(a) reacting a compound according to Formula IIA:

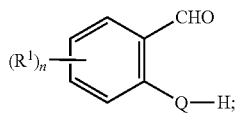

wherein $R^1$, n and Q are as defined herein;

with a compound of Formula VI:

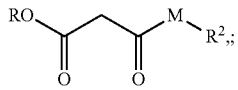

wherein $R^2$ and M are as defined herein, and R is —H or —($C_1$-$C_7$)hydrocarbyl, preferably benzyl or —($C_1$-$C_6$)alkyl, more preferably —($C_1$-$C_3$)alkyl, most preferably methyl or ethyl; and (b) isolating a compound according to Formula I from the reaction products.

According to a first sub-embodiment of the above method of preparing a compound of Formula I, there is further provided a method of preparing a compound of Formula I wherein M is (a):

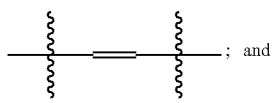

$R^1$, $R^2$, Q and n are as defined herein, said method comprising the steps of:

(a) reacting a compound according to Formula IIA:

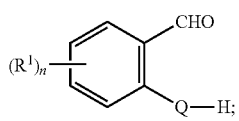

wherein $R^1$, n and Q are as defined herein;

with a compound of Formula VIB:

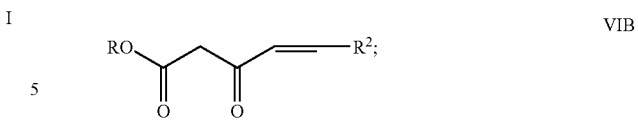

wherein $R^2$ is as defined herein, and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to a second sub-embodiment of the above method of preparing a compound of Formula I, there is further provided a method of preparing a compound of Formula I wherein M is (b):

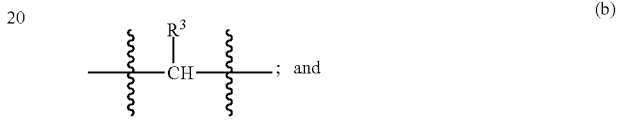

$R^1$, $R^2$, $R^3$, Q and n are as defined herein, said method comprising the steps of:

(a) reacting a compound according to Formula IIA:

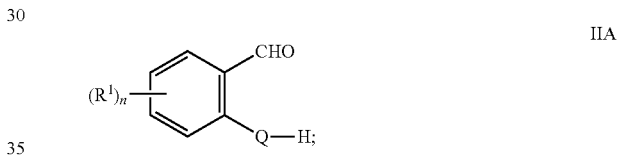

wherein $R^1$, n and Q are as defined herein;

with a compound of Formula VIC:

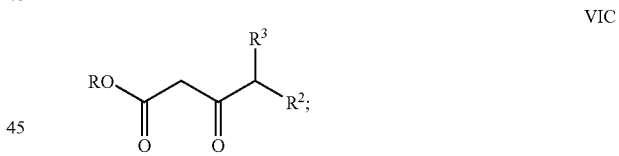

wherein $R^2$ is as defined herein, and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to another embodiment of the invention, there is provided a process of preparing a compound according to Formula I, wherein M is a single bond, said method comprising the steps of:

(a) reacting a compound according to Formula IIA:

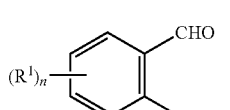

wherein $R^1$, n and Q are as defined herein;

with 3-oxopentanedioic acid:

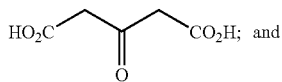

(b) isolating a compound according to Formula I from the reaction products.

According to another embodiment of the invention, there is provided a process of preparing a compound according to Formula I wherein M is (c):

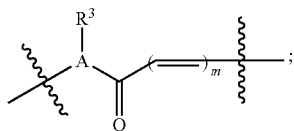

$R^3$ is as defined herein; and m is 1; said method comprising the steps of:

(a) reacting a compound according to Formula IIA:

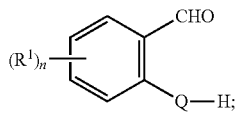

wherein $R^1$, n and Q are as defined herein;
with a compound of Formula IV:

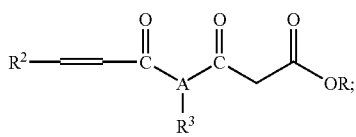

wherein $R^2$ and $R^3$ are as defined herein; and R is —H or —($C_1$-$C_7$)hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to another embodiment of the invention, there is provided a process of preparing a compound according to Formula I wherein M is (c):

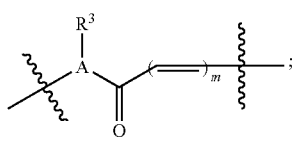

$R^3$ is as defined herein; and m is 0; said method comprising the steps of:

(a) reacting a compound according to Formula IIA:

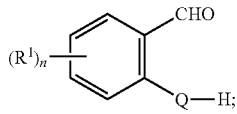

wherein $R^1$, n and Q are as defined herein;
with compound IIB:

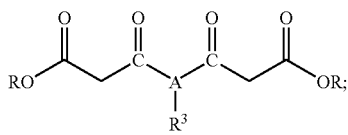

wherein $R^3$ is as defined herein; and R is —H or —($C_1$-$C_7$) hydrocarbyl, preferably benzyl or —($C_1$-$C_6$) alkyl, more preferably —($C_1$-$C_3$) alkyl, most preferably methyl or ethyl; and (b) isolating a compound according to Formula I from the reaction products.

According to another embodiment of the invention, there is provided a process of preparing a compound according to Formula I wherein M is (c):

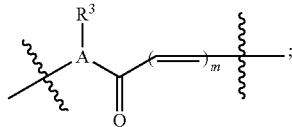

$R^3$ is as defined herein; and m is 1, said method comprising the steps of:

(a) reacting a compound according to Formula II:

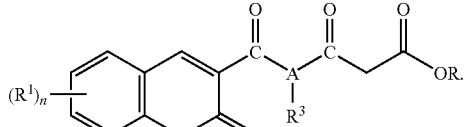

wherein each $R^1$, $R^w$, $R^x$, $R^y$, $R^z$, R, A, Q and n are as defined herein; or a salt of such a compound; with a compound of formula IVA:

wherein $R^2$ is substituted or unsubstituted aryl or substituted or unsubstituted heteroaryl;
provided that the compound according to Formula IVA is other than a compound according to Formula IIA; and (b) isolating a compound according to Formula I from the reaction products.

According to another embodiment of the invention, there is provided a process of preparing a compound according to Formula I wherein M is (c):

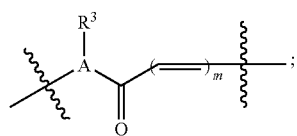

$R^3$ is as defined herein; and m is 0, said method comprising the steps of:
(a) reacting a compound according to Formula II:

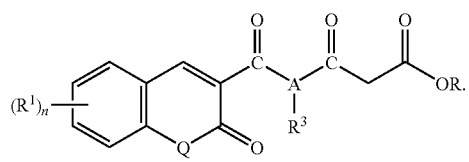

wherein A is CH and $R^1$, $R^w$, $R^x$, $R^y$, $R^z$, R, Q and n are as defined herein; or a salt of such a compound;
with a compound according to Formula IIA:

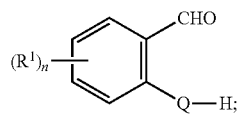

wherein $R^1$, Q and n are as defined above; and
(b) isolating a compound according to Formula I from the reaction products.

IV. Pharmaceutical Compositions and Methods of Treatment

According to another embodiment of the invention, a pharmaceutical composition is provided comprising a pharmaceutically acceptable carrier and one or more compounds according to Formula V:

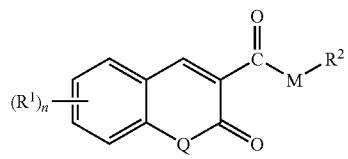

wherein:
each Q is independently O, S, or NH;
each $R^1$ is independently selected from the group consisting of halogen, —$(C_1-C_8)$hydrocarbyl, —C(=O)$R^y$, —$NR^w{}_2$, —N($R^w$)C(=O)$R^y$, —N($R^w$)CH($R^z$)C(=O)$R^y$, —N($R^w$)SO$_2R^y$, —N($R^w$)$(C_1-C_4)$alkylene-CO$_2R^w$, —NO$_2$, —CN, —$OR^w$, —OC(=O)$R^y$, —OCH($R^z$)C(=O)$R^y$, —OSO$_2R^y$, —O$(C_1-C_4)$alkylene-CO$_2R^w$, —OP(=O)(OR$^w$)$_2$, —O$(C_2-C_6)$alkylene-N(CH$_3$)$_2$, —O$(C_1-C_6)$haloalkyl, —P(=O)(OR$^w$)$_2$, —SO$_2$N($R^w$)$R^x$, —NHC(=NH)NHR$^x$, —$(C_1-C_6)$haloalkyl and heteroalkyl;

$R^w$ is —H or —$(C_1-C_8)$hydrocarbyl;
$R^x$ is —H, —$(C_1-C_8)$hydrocarbyl or —C(=O)$(C_1-C_8)$hydrocarbyl;
$R^y$ is selected from the group consisting of —H, —$(C_1-C_8)$hydrocarbyl, —O$(C_1-C_8)$hydrocarbyl, substituted phenyl, substituted heterocyclyl$(C_1-C_3)$alkyl, heteroaryl$(C_1-C_3)$alkyl, —$(C_2-C_{10})$heteroalkyl, —$(C_1-C_6)$haloalkyl, —CH($R^z$)NHR$^x$, —N($R^w$)$R^x$, —$(C_1-C_3)$alkyleneNH$_2$, —$(C_1-C_3)$alkyleneN(CH$_3$)$_2$, —$(C_1-C_3)$perfluoroalkyleneN(CH$_3$)$_2$, —$(C_1-C_3)$alkyleneN$^+$(C$_1$-C$_3$)$_3$, —$(C_1-C_3)$alkylene-N$^+$(CH$_2$CH$_2$OH)$_3$, —$(C_1-C_3)$alkylene-OR$^x$, —$(C_1-C_4)$alkylene-CO$_2R^x$, —$(C_1-C_4)$alkylene-CO$_2$N($R^w$)$R^x$, —$(C_1-C_4)$alkylene-C(=O)halogen, halo$(C_1-C_3)$alkyl and —$(C_1-C_4)$perfluoroalkylene-CO$_2R^x$;
$R^z$ is selected from the group consisting of —H, —$(C_1-C_6)$alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);
each n is independently selected from the group consisting of 0, 1, 2, 3 and 4; preferably 1, 2, 3 and 4; more preferably 1, 2 and 3;
M is selected from the group consisting of a single bond and (a), (b), and (c):

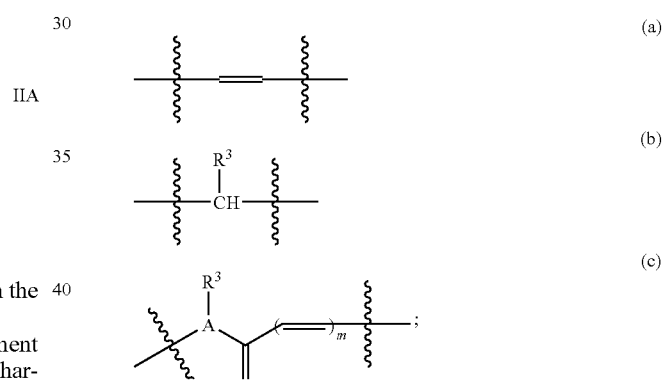

A is N or CH;
$R^2$ is substituted or unsubstituted aryl other than unsubstituted phenyl, preferably substituted aryl, more preferably substituted phenyl; or substituted or unsubstituted heteroaryl, preferably monocyclic or bicyclic heteroaryl, more preferably 5- or 6-membered ring monocyclic heteroaryl or a 9- or 10-membered bicyclic heteroaryl;
$R^3$ is selected from the group consisting of —H and —$(C_1-C_6)$alkyl, preferably —H and —CH$_3$, more preferably —H;
m is 0 or 1; and
provided that:
(i) when M is a single bond, then $R^2$ is:

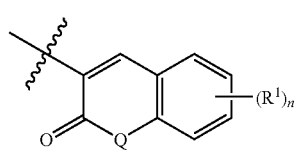

(ii) when M is (c) and m is 0, then $R^2$ is:

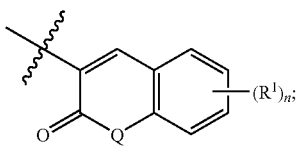

(iii) when M is (b), then n is other than O, $R^1$ is other than 7-$NR^w{}_2$, and $R^2$ is other than 4-alkoxyphenyl; and (iv) when M is (a) and Q is O, then $R^1$ is other than —$NR^w{}_2$ and n is other than 0;

or a pharmaceutically-acceptable salt of such a compound.

According to another embodiment of the invention, a method of treating an individual suffering from a proliferative disorder, particularly cancer, is provided, comprising administering to said individual an effective amount of at least one compound according to Formula I or at least one compound according to Formula V, either alone, or in combination with a pharmaceutically acceptable carrier.

According to another embodiment of the invention, a method of inhibiting growth of tumor cells in an individual suffering from a proliferative disorder, particularly cancer, is provided comprising administering to said individual an effective amount of at least one compound according to Formula I or at least one compound according to Formula V, either alone, or in combination with a pharmaceutically acceptable carrier.

According to another embodiment, a method of inducing apoptosis of cancer cells, preferably tumor cells, in an individual afflicted with cancer is provided, comprising administering to said individual an effective amount of an effective amount of at least one compound according to Formula I or at least one compound according to Formula V, either alone, or in combination with a pharmaceutically acceptable carrier.

According to another embodiment of the invention, a method of treating an individual suffering from a viral infection, particularly HIV, is provided, comprising administering to said individual an effective amount of an effective amount of at least one compound according to Formula I or at least one compound according to Formula V, either alone, or in combination with a pharmaceutically acceptable carrier.

According to another embodiment of the invention, a method of inhibiting viral replication, in an individual infected with a virus, particularly HIV, is provided, comprising administering to said individual an effective amount of an effective amount of at least one compound according to Formula I or at least one compound according to Formula V, either alone, or in combination with a pharmaceutically acceptable carrier.

According to another embodiment of the invention, a method of preventing or delaying the development of acquired immune deficiency syndrome (AIDS) in an individual infected with HIV is provided, comprising administering to said individual an effective amount of an effective amount of at least one compound according to Formula I or at least one compound according to Formula V, either alone, or in combination with a pharmaceutically acceptable carrier.

According to some preferred embodiments of the invention, the above methods comprise administration of a compound according to Formula I selected from the group consisting of: 6-bromo-3-[(6-bromo-2-oxochromen-3-yl)carbonyl]chromen-2-one; 7-methoxy-3-[(7-methoxy-2-oxochromen-3-yl)carbonyl]chromen-2-one; 5,7-dimethoxy-3-[(5,7-dimethoxy-2-oxochromen-3-yl)carbonyl]chromen-2-one; 8-ethoxy-3-[(8-ethoxy-2-oxochromen-3-yl)carbonyl]chromen-2-one; (2-oxochromen-3-yl) carbonyl]chromen-2-one; (2-oxochromen-3-yl)carbonyl]quinolin-2-one; (2-oxochromen-3-yl)carbonyl]thio-chromen-2-one; 6-chloro-3-[(6-chloro-2-oxochromen-3-yl)carbonyl]chromen-2-one; 6-fluoro-3-[(6-fluoro-2-oxochromen-3-yl)carbonyl]chromen-2-one; 6-iodo-3-[(6-iodo-2-oxochromen-3-yl)carbonyl]chromen-2-one; 6-nitro-3-[(6-nitro-2-oxochromen-3-yl)carbonyl]chromen-2-one; 8-methoxy-3-[(8-methoxy-6-nitro-2-oxochromen-3-yl)carbonyl]-6-nitrochromen-2-one; 7-hydroxy-3-[(7-hydroxy-2-oxochromen-3-yl)carbonyl]chromen-2-one; 6,8-dichloro-3-[(6,8-dichloro-2-oxochromen-3-yl)carbonyl]chromen-2-one; 6,8-dibromo-3-[(6,8-dibromo-2-oxochromen-3-yl)carbonyl]chromen-2-one; 6,8-difluoro-3-[(6,8-difluoro-2-oxochromen-3-yl)carbonyl]chromen-2-one; 5-bromo-8-methoxy-3-[(5-bromo-8-methoxy-2-oxochromen-3-yl)carbonyl]chromen-2-one; 6-bromo-8-methoxy-3-[(6-bromo-8-methoxy-2-oxochromen-3-yl)carbonyl]chromen-2-one; 8-hydroxy-3-[(8-hydroxy-2-oxochromen-3-yl)carbonyl]chromen-2-one; 6-hydroxy-3-[(6-hydroxy-2-oxochromen-3-yl)carbonyl]chromen-2-one; 6-chloro-8-bromo-3-[(6-chloro-8-bromo-2-oxochromen-3-yl)carbonyl]chromen-2-one; [(2-oxobenzo[g]chromen-3-yl)carbonyl]benzo[g]chromen-2-one; 5-methoxy-3-[(5-methoxy-2-oxochromen-3-yl)carbonyl]-chromen-2-one; 6-methyl-3-[(6-methyl-2-oxochromen-3-yl)carbonyl]chromen-2-one; 6-trifluoromethoxy-3-[(6-trifluoromethoxy-2-oxochromen-3-yl)carbonyl]chromen-2-one; 8-nitro-3-[(8-nitro-2-oxochromen-3-yl)carbonyl]chromen-2-one; 6-bromo-8-nitro-3-[(6-bromo-8-nitro-2-oxochromen-3-yl)carbonyl]chromen-2-one; 8-fluoro-3-[(8-fluoro-2-oxo-chromen-3-yl)carbonyl]chromen-2-one; 6-nitro-8-bromo-3-[(6-nitro-8-bromo-2-oxochromen-3-yl)carbonyl]chromen-2-one; and 6,8-dinitro-3-[(6,8-dinitro-2-oxochromen-3-yl)carbonyl]chromen-2-one; mixtures thereof; and pharmaceutically acceptable salts thereof.

According to other embodiments of the invention, there is provided the use of at least one compound according to Formula I, or at least one compound according to Formula V, for preparation of a medicament for:

(a) treating a proliferative disorder in an individual afflicted with a proliferative disorder;

(b) inhibiting the growth of tumor cells in an individual afflicted with a proliferative disorder;

(c) inducing apoptosis of cancer cells in an individual afflicted with cancer;

(d) treating a viral disorder in an individual afflicted with a viral disorder;

(e) inhibiting viral replication in an individual infected with a virus; or (f) preventing or delaying the development of AIDS in an individual infected with HIV.

DETAILED DESCRIPTION OF THE INVENTION

I. Treatment of Proliferative Disorders

According to the present invention, certain 3-acylcoumarins 3-acylthiochromene-2-ones and 3-acyl-2-quinolones selectively kill various tumor cell types without killing normal cells. Without wishing to be bound by any theory, it is believed that the compounds are inhibitors of cyclin dependent kinases, and thereby affect tumor cell growth and viability.

A. Treatment of Cancer

The compounds according to the invention may be administered to individuals, particularly mammals, including animals and humans, afflicted with a proliferative disorder such as cancer. The compounds according to the invention are believed to inhibit the proliferation of tumor cells. The activity of the compounds according to the invention is selective for tumor cells over normal cells.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Karposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers including, for example, malignant melanoma, basal cell carcinoma, squamous cell carcinoma, Karposi's sarcoma, moles dysplastic nevi, lipoma, angioma, dermatofibroma, keloids, psoriasis; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified disorders.

B. Treatment of Non-Cancer Proliferative Disorders

The compounds are also believed useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Non-cancer proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Pagets Disease of the bone, fibrocystic disease of the breast, uterine fibroids, Peronies and Duputren's fibrosis, restenosis, benign proliferative breast disease, benign prostatic hyperplasia, X-linked lymphoproliferative disorder (Duncan disease), post-transplantation lymphoproliferative disorder (PTLD), macular degeneration, and retinopathies, such as diabetic retinopathies and proliferative vitreoretinopathy (PVR).

Other non-cancer proliferative disorders believed treatable by compounds according to the invention include the presence of pre-cancerous lymphoproliferative cells associated with an elevated risk of progression to a cancerous disorder. Many non-cancerous lymphoproliferative disorders are associated with latent viral infections such as Epstein-Barr virus (EBV) and Hepatitis C. These disorders often begin as a benign pathology and progress into lymphoid neoplasia as a function of time. Treatment of tumor cells with the compounds according to the invention is believed to lead to inhibition of cell proliferation and induction of apoptotic cell death.

C. Treatment of Disorders Associated with CDK9

Compounds according to the invention inhibit CDK9. Inhibition of CDK9 serves to inhibit CDK9 mediated activation of Tat, which activation is required to promote proliferation and thereby facilitate viral replication. Inhibition of CDK9 has also been shown to inhibit replication of other viruses including varicella-zoster virus and herpes simplex. The compounds of the invention are therefore believed to be useful in the treatment of viral infections such as, for example, herpevirus, poxyvirus, Epstein-Barr virus, Sindbis virus, HIV varicella-zoster virus and adenovirus. The compounds of the invention are further believed to inhibit viral replication and thereby to be useful in preventing the development of AIDS in individuals who are infected with HIV.

II. Isomerism in Compounds of the Invention

A. Geometric Isomerism

Some compounds according to Formula I are characterized by isomerism resulting from the presence of a carbon-carbon double bond. This isomerism is commonly referred to as cis-trans isomerism, but the more comprehensive naming convention employs E- and Z-designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4$^{th}$ ed., 1992, p. 127-138, the entire contents of which is incorporated herein by reference. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus, if the four groups on a carbon-carbon double bond are ranked, A being the lowest rank and D being highest, A>B>C>D, the isomers would be named as in Scheme 3.

Scheme 3

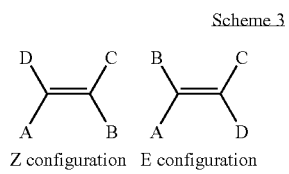

Z configuration   E configuration

Unless otherwise indicated, both configurations, as depicted below in Scheme 4, and mixtures thereof, are included in the scope of compounds according to Formula I.

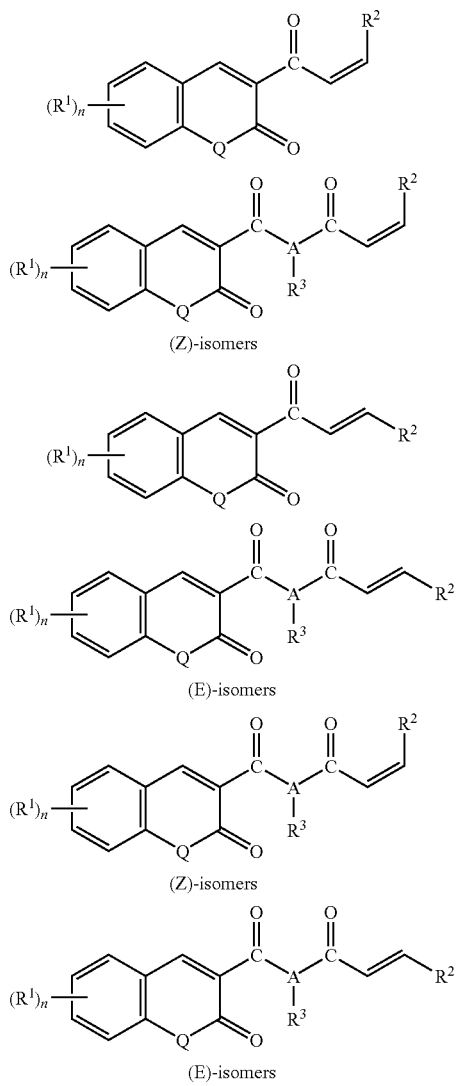

C. Optical Isomerism

The present invention is also directed to isolated optical isomers of compounds according to Formula I. The isomers resulting from the presence of a chiral center comprise a pair of non-superimposable isomers that are called "enantiomers". Single enantiomers of a pure compound are optically active, i.e., they are capable of rotating the plane of plane polarized light. Single enantiomers are designated according to the Cahn-Ingold-Prelog system. See March, Advanced Organic Chemistry, 4$^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 7, the Cahn-Ingold-Prelog ranking is A>B>C>D. The lowest ranking atom, D is oriented away from the viewer.

Scheme 5

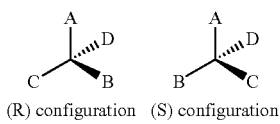

(R) configuration   (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

By "isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL CHIRALPAK family of columns (Daicel Chemical Industries, Ltd., Tokyo, Japan). The column is operated according to the manufacturer's instructions.

III. Preparation of Compounds According to the Invention

Compounds according to Formula I may be prepared via synthetic organic chemistry methods as follows.

A. Preparation of Ketones of Formula I

Compounds of Formula I wherein M is (a):

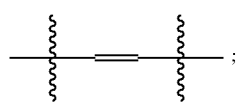

may be prepared according to the methods depicted in Scheme 6 by reacting an intermediate benzaldehyde 4, with either intermediate 8a or intermediate 8b.

Scheme 6

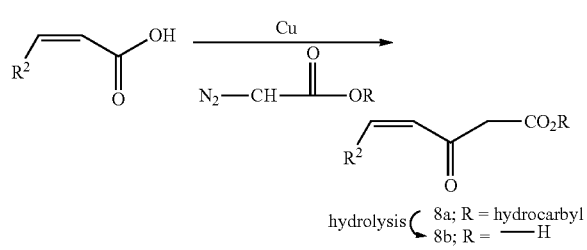

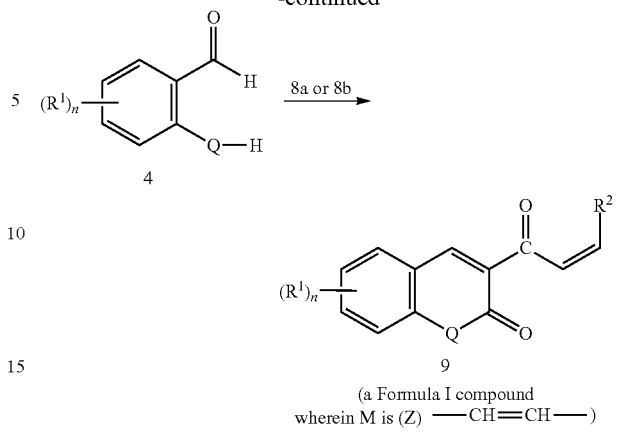

(a Formula I compound
wherein M is (Z) ——CH══CH——)

According to Scheme 6, the Z-olefin 8a may be prepared from the corresponding Z-carboxylic acid (e.g., a Z-cinnamic acid) by reaction with a diazoacetate, preferably an alkyl diazoacetate (e.g., ethyl diazoacetate CA [623-73-4]. The resulting intermediate 8a may optionally be hydrolyzed. Either of Z-olefins, 8a or 8b may be reacted with a substituted 2-hydroxy (or 2-amino or 2-mercapto) benzaldehyde 4 in glacial acetic acid in the presence of a catalytic amount of benzylamine to yield compound 9.

Compounds of Formula I wherein M is a single bond may be prepared according to the methods depicted in Scheme 7 by reacting an intermediate benzaldehyde 4, with intermediate 12a or 12b.

Scheme 7

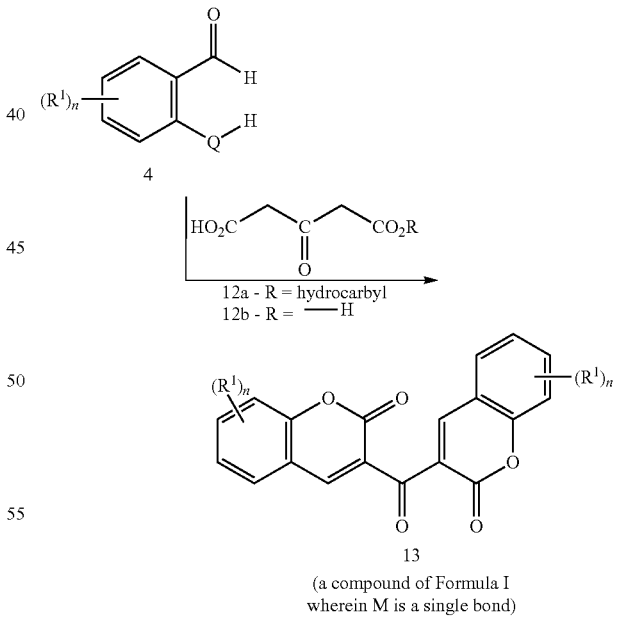

(a compound of Formula I
wherein M is a single bond)

According to Scheme 7, 1,3-acetonedicarboxylic acid [542-05-2], ACROS catalog No. AC17315 or an ester thereof (for example, dimethyl 1,3-acetonedicarboxylate 2-chloroacetic acid (CAS [1830-54-2], ACROS catalog #AC11570) may be reacted with a substituted 2-hydroxy (or 2-amino or 2-mercapto) benzaldehyde 4 in glacial acetic acid in the presence of a catalytic amount of benzylamine to yield 13. Compound 13 is shown in Scheme 8 as a symmetrical compound, however substituents R¹ on the heteroaryl rings are not required to be identical. The reaction may be modified to produce asymmetric products, i.e., wherein the two R¹ substituents are not identical, by employing two differently substituted aldehyde reagents 4. The reaction product will comprise a mixture of symmetrically substituted and asymmetrically substituted compounds. The product mixture may be separated by a suitable separation procedure. Suitable separation procedures include crystallization, column chromatography and preparative high performance liquid chromatography (HPLC).

Compounds of Formula I wherein M is (b):

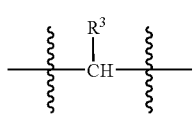

(b)

may be prepared according to the methods depicted in Scheme 8 by reacting an intermediate benzaldehyde 4, with either intermediate 16a or intermediate 16b.

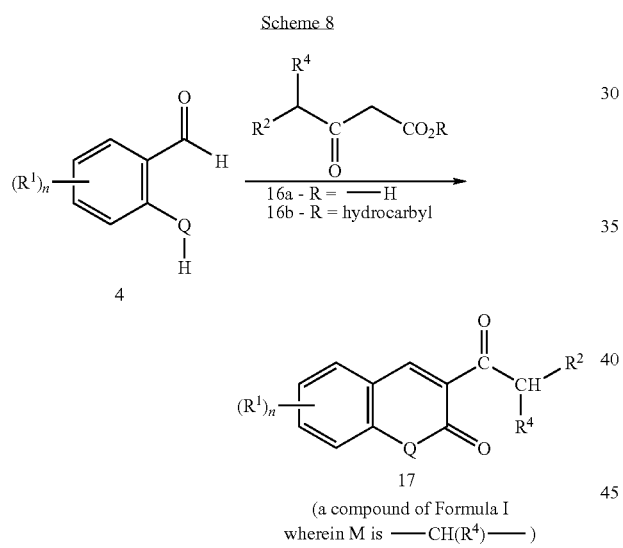

According to Scheme 8, the β-ketoacid 16a, or the β-ketoester 16b may be reacted with a substituted 2-hydroxy (or 2-amino or 2-mercapto) benzaldehyde 4 in glacial acetic acid in the presence of a catalytic amount of benzylamine to yield the compound 17.

Compounds of Formula I wherein M is (c):

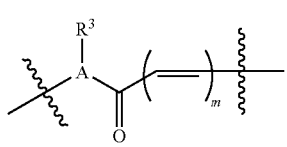

(c)

may be prepared according to the methods depicted in Scheme 9 by reacting an intermediate benzaldehyde 4, with either intermediate 20 or intermediate 21.

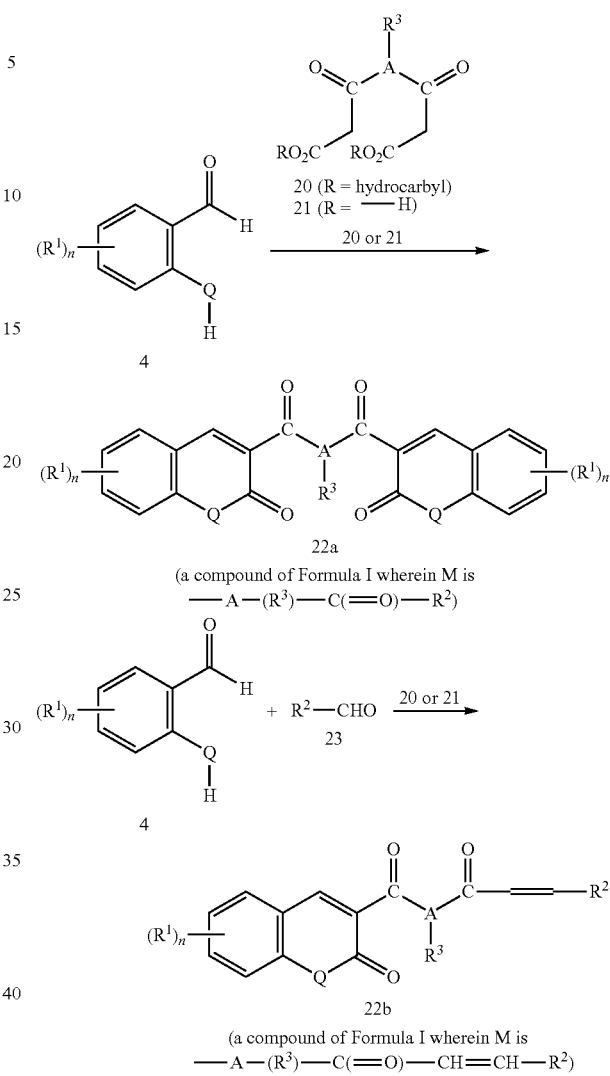

The intermediate 20 may be optionally reacted with a suitable hydrocarbyl alcohol, preferably in the presence of an acid catalyst, to form the diester, 2, wherein R is a hydrocarbyl group. Suitable hydrocarbyl alcohols include benzyl alcohols and $(C_1-C_6)$alkyl alcohols. Suitable acid catalysts for the esterification reaction include, for example, sulfuric, methane sulfonic, toluene sulfonic and hydrochloric acids.

Either of the intermediates, 20 or 21 may be reacted with a substituted 2-hydroxy (or 2-amino or 2-mercapto) benzaldehyde 4 in glacial acetic acid in the presence of a catalytic amount of benzylamine to yield bis compound 22a. Compound 22a is shown in Scheme 10 as a symmetrical compound, but substituents R¹ on the two heteroaryl rings are not required to be identical. The reaction may be modified to produce asymmetric products, i.e., wherein the two R¹ substituents are not equivalent, by employing two differently substituted aldehyde reagents 4 in the reaction to form a mixture of symmetrically substituted and asymmetrically substituted compounds, 22a. The product mixture may be separated by a suitable separation procedure. Suitable separation procedures include crystallization, column chromatography and preparative (HPLC).

Also, as shown in Scheme 9, the asymmetric compound 22b may be prepared by reacting either of 20 or 21 with a combination of substituted 2-hydroxy (or 2-amino or 2-mercapto) benzaldehyde 4 and a second aromatic aldehyde 23. This reaction will form a mixture of symmetric and asymmetric compounds, of which, the asymmetric compound, 22b, is the desired product. The product mixture may be separated by a suitable separation procedure. Suitable separation procedures for isolating the compounds 22b include crystallization, column chromatography and preparative high performance liquid chromatography (HPLC).

IV. Salts of Compounds According to the Invention

The compounds of the present invention may take the form of salts. The term "salts", embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, salicyclic, salicyclic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, toluenesulfonic, sulfanilic, cyclohexylaminosulfonic, stearic, alginic, γ-hydroxybutyric, salicyclic, galactaric and galacturonic acid. Examples of pharmaceutically unacceptable acid addition salts include, for example, perchlorates and tetrafluoroborates.

Suitable pharmaceutically-acceptable base addition salts of compounds of the invention include, for example, metallic salts, e.g., alkali metal, alkaline earth metal and transition metal salts such as, for example, calcium, magnesium, potassium, sodium and zinc salts. Pharmaceutically-acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. These salts may be prepared by conventional means from the corresponding compound of Formula I by reacting, for example, the appropriate acid or base with the Formula I compound.

V. Administration of Compounds of the Invention

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

One or more compounds useful in the practice of the present inventions may be administered simultaneously, by the same or different routes, or at different times during treatment.

The specific dose of a compound according to the invention to obtain therapeutic benefit for treatment of a proliferative disorder will, of course, be determined by the particular circumstances of the individual patient including, the size, weight, age and sex of the patient, the nature and stage of the proliferative disorder, the aggressiveness of the proliferative disorder, and the route of administration of the compound.

For example, a daily dosage of from about 0.05 to about 50 mg/kg/day may be utilized. In one embodiment, the dose is from about 1 to about 40 mg/kg/day. According to another embodiment, the does is from about 3 to about 30 mg/kg/day. Higher or lower doses are also contemplated.

The daily dose of the compound of Formula I may be given in a single dose, or may be divided, for example into two, three, or four doses, equal or unequal, but preferably equal, that comprise the daily dose. When given intravenously, such doses may be given as a bolus dose injected over, for example, about 1 to about 4 hours.

In the treatment of acute viral infection in mammals such as HIV, the compound should be administered at an effective dose sufficient to suppress viral replication. In such embodiments, dosages of about 100 to about 1000 milligrams of compound are administered orally every six hours to a subject for treatment of viral infection, e.g. HIV infection.

VI. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The practice of the invention is illustrated by the following non-limiting examples.

EXAMPLES

Examples 1-29

Synthesis of bis-Coumarin Ketone Compounds According to Formula I

General Procedures:

Method A: To a hot solution of dimethyl 1,3-acetone dicarboxylate (7.75 mmol) and catalytic amount of piperidine (200 µL) in ethanol (15 mL) was added a substituted salicylaldehyde (15.5 mmol). The resulting mixture was heated at reflux temperature for 5-40 min. The hot mixture was then cooled to ambient temperature (25° C.). A solid precipitate formed. The solid precipitate was separated by filtration and washed with cold (OC) ethanol (3×10 mL) and petroleum ether (3×10 mL) to yield the desired product.

Method B: 1,3-Acetone dicarboxylic acid (7.75 mmol), a substituted salicylaldehyde (15.5 mmol) and a catalytic amount (200 µL) of benzyl amine were dissolved in 15 mL glacial acetic acid. The resulting mixture was heated to reflux temperature and maintained at reflux temperature for 5-8 h. The hot mixture is then cooled to ambient temperature (25° C.). A solid precipitate formed. The solid precipitate was separated by filtration and washed with isopropanol (3×15 mL) to yield the desired product. In many cases the condensed product comes out of the solution, which was filtered, washed with 2-propanol (3×15 mL) to get the pure product.

Table 1 lists the reaction yields and measured melting point (M.P.) for the compounds of Examples 1-29 made according to Method A.

TABLE 1

Compounds of Examples 1-29

| Example #/Name | $R^1$ | $R^2$ | M.P. (° C.) | Yield (%) |
|---|---|---|---|---|
| Example 1: 6-bromo-3-[(6-bromo-2-oxo-chromen-3-yl)carbonyl]chromen-2-one | 6-Br | 6-bromo-coumarin-3-yl | 316-18 | 84.1 |
| Example 2: 7-methoxy-3-[(7-methoxy-2-oxochromen-3-yl)carbonyl]chromen-2-one | 7-OMe | 7-methoxy-coumarin-3-yl | 262-64 | 84.4 |
| Example 3: 5,7-dimethoxy-3-[(5,7-dimethoxy-2-oxochromen-3-yl)carbonyl]chromen-2-one | 5,7-OMe | 5,7-dimethoxy-coumarin-3-yl | 294-96 | 79.4 |
| Example 4: 8-ethoxy-3-[(8-ethoxy-2-oxochromen-3-yl)carbonyl]chromen-2-one; | 8-OEt | 8-ethoxy-coumarin-3-yl | 264-66 | 92.1 |
| Example 5: (2-oxochromen-3-yl) carbonyl]-chromen-2-one; | —H | coumarin-3-yl | 246-48 | 82 |
| Example 6: 6-chloro-3-[(6-chloro-2-oxochromen-3-yl)carbonyl]chromen-2-one; | 6-Cl | 6-chloro-coumarin-3-yl | 318-20 | 87.7 |
| Example 7: 6-fluoro-3-[(6-fluoro-2-oxochromen-3-yl)carbonyl]chromen-2-one | 6-F | 6-fluoro-coumarin-3-yl | 306-08 | 73.9 |
| Example 8: 6-iodo-3-[(6-iodo-2-oxochromen-3-yl)carbonyl]chromen-2-one | 6-I | 6-iodo-coumarin-3-yl | 272-74 | 85.4 |
| Example 9: 6-nitro-3-[(6-nitro-2-oxochromen-3-yl)carbonyl]chromen-2-one | $6-NO_2$ | 6-nitro-coumarin-3-yl | 298-00 | 64.1 |
| Example 10: 8-methoxy-3-[(8-methoxy-6-nitro-2-oxo-chromen-3-yl)carbonyl]-6-nitro-chromen-2-one | $6-NO_2$ 8-OMe | 6-nitro-8-methoxy-coumarin-3-yl | 294-96 | 78.1 |
| Example 11: 7-hydroxy-3-[(7-hydroxy-2-oxo-chromen-3-yl)carbonyl]chromen-2-one | 7-OH | 7-hydroxy-coumarin-3-yl | 216-18 | 74.6 |
| Example 12: 6,8-dichloro-3-[(6,8-dichloro-2-oxochromen-3-yl)carbonyl]chromen-2-one | $6,8-Cl_2$ | 6,8-dichloro coumarin-3-yl | 246-48 | 66.2 |
| Example 13: 6,8-dibromo-3-[(6,8-dibromo-2-oxochromen-3-yl)carbonyl]chromen-2-one | $6,8-Br_2$ | 6,8-dibromo coumarin-3-yl | 280-82 | 73.3 |
| Example 14: 6,8-difluoro-3-[(6,8-difluoro-2-oxochromen-3-yl)carbonyl]chromen-2-one | $6,8-F_2$ | 6,8-difluoro coumarin-3-yl | 266-68 | 70.3 |
| Example 15: 5-bromo-8-methoxy-3-[(5-bromo-8-methoxy-2-oxochromen-3-yl)-carbonyl]chromen-2-one | 5-Br-8-OMe | 5-Br-8-methoxy coumarin-3-yl | 332-34 | 87.7 |
| Example 16: 6-bromo-8-methoxy-3-[(6-bromo-8-methoxy-2-oxochromen-3-yl)-carbonyl]chromen-2-one | 6-Br-8-OMe | 6-Br-8-methoxy coumarin-3-yl | 338-40 | 71.4 |
| Example 17: 8-hydroxy-3-[(8-hydroxy-2-oxochromen-3-yl)carbonyl]chromen-2-one | 8-OH | 8-hydroxy-coumarin-3-yl | 356-58 | 87.1 |
| Example 18: 6-hydroxy-3-[(6-hydroxy-2-oxochromen-3-yl)carbonyl]chromen-2-one | 6-OH | 6-hydroxy-coumarin-3-yl | 340-42 | 74.6 |

TABLE 1-continued

Compounds of Examples 1-29

| Example #/Name | R¹ | R² | M.P. (° C.) | Yield (%) |
|---|---|---|---|---|
| Example 19: 6-chloro-8-bromo-3-[(6-chloro-8-bromo-2-oxochromen-3-yl)carbonyl]-chromen-2-one | 6-Cl-8-Br | 6-chloro-8-bromo-coumarin-3-yl | 266-68 | 73.5 |
| Example 20: [(2-oxobenzo[g]chromen-3-yl)-carbonyl]benzo[g]chromen-2-one | 6,7-benzo | benzo-coumarin-3-yl | 370-72 | 81.2 |
| Example 21: 5-methoxy-3-[(5-methoxy-2-oxochromen-3-yl)carbonyl]chromen-2-one | 5-Ome | 5-methoxy coumarin-3-yl | 270-72 | 92 |
| Example 22: 6-methyl-3-[(6-methyl-2-oxochromen-3-yl)carbonyl]chromen-2-one | 6-Me | 6-methyl coumarin-3-yl | 270-72 | 70.5 |
| Example 23: 6-trifluoromethoxy-3-[(6-trifluoromethoxy-2-oxochromen-3-yl)-carbonyl]chromen-2-one | 6-OCF₃ | 6-OCF₃ coumarin-3-yl | 266-68 | 57.3 |
| Example 24: 8-nitro-3-[(8-nitro-2-oxo-chromen-3-yl)carbonyl]chromen-2-one | 8-NO₂ | 8-nitro coumarin-3-yl | 204-06 | 68.3 |
| Example 25: 6-bromo-8-nitro-3-[(6-bromo-8-nitro-2-oxochromen-3-yl)carbonyl]-chromen-2-one | 6-Br-8-NO₂ | 6-bromo-8-nitro coumarin-3-yl | 214-16 | 67.7 |
| Example 26: 8-fluoro-3-[(8-fluoro-2-oxochromen-3-yl)carbonyl]chromen-2-one | 8-F | 8-fluoro coumarin-3-yl | 288-90 | 72.7 |
| Example 27: 6-nitro-8-bromo-3-[(6-nitro-8-bromo-2-oxochromen-3-yl)carbonyl]-chromen-2-one | 6-NO₂-8-Br | 6-nitro-8-bromo coumarin-3-yl | 150-52 | 71.7 |
| Example 28: 6,8-dinitro-3-[(6,8-dinitro-2-oxochromen-3-yl)carbonyl]chromen-2-one | 6,8-(NO₂)₂ | 6,8-dinitro coumarin-3-yl | 192-94 | 69.9 |
| Example 29: 6,8-diiodo-3-[(6,8-diiodo-2-oxochromen-3-yl)carbonyl]chromen-2-one | 6,8-I₂ | 6,8-diiodo coumarin-3-yl | 327-330 | 59.3 |

Example 30

Effect of Compounds of Formula I on Tumor Cell Lines

A. Cells.

The effect of compounds according to Formula I on the growth of human tumor cells in culture was evaluated using the androgen receptor negative prostate cell line DU145. All cell cultures were maintained at 37° C. in a humidified atmosphere of 5% $CO_2$.

B. Treatment of Cells with Compounds According to Formula I

Cells were treated with compounds according to Formula I at five different concentrations (1-100 μM range) for each compound. The dose response of each cell line was established by determining the number of viable cells after 96 h of continuous treatment against each of the different test concentrations of each compound. The determination of viable cells was done by the by the Trypan blue exclusion method. An $IC_{50}$ (μM) for each compound was determined. The results appear in Table 2.

TABLE 2

Cytotoxicity of Compounds on DU145 Cells

| Example #/Name | R¹ | R² | $IC_{50}$ (μM) |
|---|---|---|---|
| Example 1: 6-bromo-3-[(6-bromo-2-oxo-chromen-3-yl)carbonyl]chromen-2-one | 6-Br | 6-bromo-coumarin-3-yl | 100 |
| Example 2: 7-methoxy-3-[(7-methoxy-2-oxochromen-3-yl)carbonyl]chromen-2-one | 7-OMe | 7-methoxy-coumarin-3-yl | 100 |
| Example 3: 5,7-dimethoxy-3-[(5,7-dimethoxy-2-oxochromen-3-yl)-carbonyl]chromen-2-one | 5,7-OMe | 5,7-di-methoxy-coumarin-3-yl | 100 |
| Example 4: 8-ethoxy-3-[(8-ethoxy-2-oxochromen-3-yl)carbonyl]chromen-2-one;; | 8-OEt | 8-ethoxy-coumarin-3-yl | 100 |
| Example 5: (2-oxochromen-3-yl)carbonyl]-chromen-2-one; | —H | coumarin-3-yl | 100 |
| Example 6: 6-chloro-3-[(6-chloro-2-oxochromen-3-yl)carbonyl]chromen-2-one; | 6-Cl | 6-chloro-coumarin-3-yl | 100 |
| Example 7: 6-fluoro-3-[(6-fluoro-2-oxochromen-3-yl)carbonyl]chromen-2-one | 6-F | 6-fluoro-coumarin-3-yl | 100 |
| Example 8: 6-iodo-3-[(6-iodo-2-oxochromen-3-yl)carbonyl]chromen-2-one | 6-I | 6-iodo-coumarin-3-yl | 100 |
| Example 9: 6-nitro-3-[(6-nitro-2-oxochromen-3-yl)carbonyl]chromen-2-one | 6-NO₂ | 6-nitro-coumarin-3-yl | 1-10 |
| Example 10: 8-methoxy-3-[(8-methoxy-6-nitro-2-oxo-chromen-3-yl)carbonyl]-6-nitro-chromen-2-one | 6-NO₂-8-OMe | 6-nitro-8-methoxy-coumarin-3-yl | 10-25 |
| Example 11: 7-hydroxy-3-[(7-hydroxy-2-oxo-chromen-3-yl)carbonyl]chromen-2-one | 7-OH | 7-hydroxy-coumarin-3-yl | 100 |
| Example 12: 6,8-dichloro-3-[(6,8-dichloro-2-oxochromen-3-yl)carbonyl]chromen-2-one | 6,8-Cl₂ | 6,8-dichloro coumarin-3-yl | 10-25 |
| Example 13: 6,8-dibromo-3-[(6,8-dibromo-2-oxochromen-3-yl)carbonyl]chromen-2-one | 6,8-Br₂ | 6,8-dibromo coumarin-3-yl | 10-25 |
| Example 14: 6,8-difluoro-3-[(6,8-difluoro-2-oxochromen-3-yl)carbonyl]chromen-2-one | 6,8-F₂ | 6,8-difluoro coumarin-3-yl | 10-25 |
| Example 15: 5-bromo-8-methoxy-3-[(5-bromo-8-methoxy-2-oxochromen-3-yl)-carbonyl]chromen-2-one | 5-Br-8-OMe | 5-Br-8-methoxy coumarin-3-yl | 25-50 |
| Example 16: 6-bromo-8-methoxy-3-[(6-bromo-8-methoxy-2-oxochromen-3-yl)-carbonyl]chromen-2-one | 6-Br-8-OMe | 6-Br-8-methoxy coumarin-3-yl | 50-100 |
| Example 17: 8-hydroxy-3-[(8-hydroxy-2-oxochromen-3-yl)carbonyl]chromen-2-one | 8-OH | 8-hydroxy-coumarin-3-yl | 25-50 |
| Example 18: 6-hydroxy-3-[(6-hydroxy-2-oxochromen-3-yl)carbonyl]chromen-2-one | 6-OH | 6-hydroxy-coumarin-3-yl | 100 |
| Example 19: 6-chloro-8-bromo-3-[(6-chloro-8-bromo-2-oxochromen-3-yl)carbonyl]chromen-2-one | 6-Cl-8-Br | 6-chloro-8-bromo-coumarin-3-yl | 1-10 |

TABLE 2-continued

Cytotoxicity of Compounds on DU145 Cells

| Example #/Name | $R^1$ | $R^2$ | $IC_{50}$ (μM) |
|---|---|---|---|
| Example 20: [(2-oxobenzo[g]chromen-3-yl)-carbonyl]benzo[g]chromen-2-one | 6,7-benzo | benzo-coumarin-3-yl | 25-50 |
| Example 21: 5-methoxy-3-[(5-methoxy-2-oxochromen-3-yl)carbonyl]chromen-2-one | 5-Ome | 5-methoxy coumarin-3-yl | 50-100 |
| Example 22: 6-methyl-3-[(6-methyl-2-oxochromen-3-yl)carbonyl]chromen-2-one | 6-Me | 6-methyl coumarin-3-yl | ND |
| Example 23: 6-trifluoromethoxy-3-[(6-tri-fluoromethoxy-2-oxochromen-3-yl)-carbonyl]chromen-2-one | 6-OCF$_3$ | 6-OCF$_3$ caumarin-3-yl | ND |
| Example 24: 8-nitro-3-[(8-nitro-2-oxo-chromen-3-yl)carbonyl]chromen-2-one | 8-NO$_2$ | 8-nitro coumarin-3-yl | ND |
| Example 25: 6-bromo-8-nitro-3-[(6-bromo-8-nitro-2-oxochromen-3-yl)carbonyl]-chromen-2-one | 6-Br 8-NO$_2$ | 6-bromo-8-nitro coumarin-3-yl | ND |
| Example 26: 8-fluoro-3-[(8-fluoro-2-oxochromen-3-yl)carbonyl]chromen-2-one | 8-F | 8-fluoro coumarin-3-yl | ND |
| Example 27: 6-nitro-8-bromo-3-[(6-nitro-8-bromo-2-oxochromen-3-yl)carbonyl]-chromen-2-one | 6-NO$_2$-8-Br | 6-nitro-8-bromo coumarin-3-yl | ND |
| Example 28: 6,8-dinitro-3-[(6,8-dinitro-2-oxochromen-3-yl)carbonyl]chromen-2-one | 6,8-(NO$_2$)$_2$ | 6,8-dinitro coumarin-3-yl | ND |
| Example 29: 6,8-diiodo-3-[(6,8-diiodo-oxochromen-3-yl)carbonyl]chromen-2-one | 6,8-I$_2$ | 6,8-diiodo coumarin-3-yl | 10-20 |

ND = Not done.

Following the same protocol, other tumor cell lines may be tested, such as colorectal (DLD-1), non-small cell lung carcinoma (H157), estrogen breast (BT20) and chronic myeloid leukemia (K562) cell lines.

Example 31

Inhibition of CDKs in In Vitro Kinase Assay

One unit of CDK1/CyclinB, CDK2/CylinE, CDK4/CyclinD1 or CDK9/CyclinT1 recombinant human enzyme complex was incubated with various concentrations of compounds of the invention for 30 min at RT. CDK1/CyclinB, CDK2/CylinE and CDK9/CyclinT1 were obtained from Upstate USA Charlottesville, Va. CDK4/CyclinD1 was obtained from SignaGen Laboratories, Gaithersburg, Md. After incubation, a kinase reaction was performed at 300° C. for 20 min in the presence of 100 mM ATP, 40 mCi g32pATP and 1 mg of the following as substrate: Histone H1, for CDK1 and CDK2; the carboxy terminal domain of the fusion protein glutathione S-transferase-retinoblastoma (GST-Rb), for CDK4; or RNA Polymerase II carboxy terminal domain, for CDK9. The reaction was terminated by addition of 0.25 mM EDTA and spotted on P81 phospho cellulose filters. The filters were washed thrice for 5 min each with 0.75% phosphoric acid and once with acetone. The filters were transferred to a scintillation vial and incorporation of radioactive label was determined with a scintillation counter.

Data for the kinase assays represent an average of two independent experiments, each of which was performed in triplicate. The IC$_{50}$ for each tested compound was obtained by plotting the percentage of total radioactive counts incorporated into the substrate at selected concentrations of compounds according to the invention compared with total counts incorporated in the absence of the compound. The inhibitory activity by the tested compounds against CDK1, CDK2, CDK4 and CDK9 is shown below in Table 3.

TABLE 3

CDK Inhibition of Compounds of Formula I

| Compound of Example # | CDK1 IC$_{50}$ (μM) | CDK2 IC$_{50}$ (μM) | CDK4 IC$_{50}$ (μM) | CDK9 IC$_{50}$ (μM) |
|---|---|---|---|---|
| 1 | >10 | ND | >10 | ND |
| 2 | >10 | ND | >10 | ND |
| 3 | >10 | ND | >10 | ND |
| 4 | >10 | ND | >10 | ND |
| 5 | >10 | ND | >10 | ND |
| 6 | 1.0-10.0 | ND | >10 | ND |
| 7 | >10 | ND | >10 | ND |
| 8 | >10 | ND | >10 | ND |
| 9 | >10 | 1.54 | >10 | 0.5 |
| 10 | >10 | 0.549 | >10 | 0.5 |
| 11 | >10 | ND | >10 | ND |
| 12 | >10 | ND | 2.5-5.0 | ND |
| 13 | ND | 10 | 2.5-5.0 | 0.5 |
| 14 | >10 | ND | >10 | ND |
| 15 | >10 | ND | >10 | ND |
| 16 | >10 | ND | >10 | ND |
| 17 | >10 | ND | >10 | ND |
| 18 | >10 | ND | >10 | ND |
| 19 | 1.0-10.0 | 0.089 | >10 | 0.5 |
| 20 | >10 | ND | >10 | ND |
| 21 | >10 | 10 | >10 | 0.5 |
| 22 | 1.0-10.0 | ND | >10 | ND |
| 23 | >10 | ND | >10 | ND |
| 24 | >10 | ND | >10 | ND |
| 25 | ND | ND | ND | ND |
| 26 | >10 | ND | >10 | ND |
| 27 | ND | ND | >10 | ND |
| 28 | ND | ND | >10 | ND |
| 29 | ND | ND | 0.04 | ND |

ND = Not done.

All references cited herein are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:
1. A compound according to Formula I:

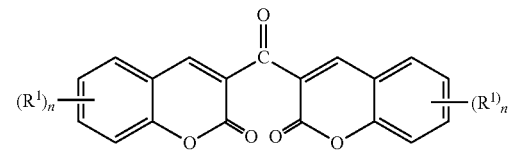

wherein:
each $R^1$ is independently selected from the group consisting of halogen, —C(=O)R$^y$, —NR$^w_2$, —N(R$^w$)C(=O)R$^y$, —N(R$^w$)CH(R$^z$)C(=O)R$^y$, —N(R$^w$)SO$_2$R$^y$, —NO$_2$, —CN, —OCH(R$^z$)C(=O)R$^y$, —OSO$_2$R$^y$—O(C$_1$-C$_4$)alkylene-CO$_2$R$^w$, —OP(=O)(OR$^w$)$_2$, —O(C$_2$-C$_6$)alkylene-N(CH$_3$)$_2$, —P(=O)(OR$^w$)$_2$, —SO$_2$N(R$^w$)R$^x$ and —NHC(=NH)NHR$^x$;

R$^w$ is —H or —(C$_1$-C$_8$)hydrocarbyl;

R$^x$ is —H, —(C$_1$-C$_8$)hydrocarbyl or —C(=O)(C$_1$-C$_8$)hydrocarbyl;

$R^y$ is selected from the group consisting of —H, —($C_1$-$C_8$) hydrocarbyl, —O($C_1$-$C_8$)hydrocarbyl, substituted phenyl, substituted heterocyclyl($C_1$-$C_3$)alkyl, heteroaryl ($C_1$-$C_3$)alkyl, —($C_2$-$C_{10}$)heteroalkyl, —($C_1$-$C_6$) haloalkyl, —CH($R^z$)NHR$^x$, —N(R$^w$)R$^x$, —($C_1$-$C_3$) alkyleneNH$_2$, —($C_1$-$C_3$)alkyleneN(CH$_3$)$_2$, —($C_1$-$C_3$) perfluoroalkyleneN(CH$_3$)$_2$, —($C_1$-$C_3$)alkyleneN$^+$($C_1$-$C_3$)$_3$, —($C_1$-$C_3$)alkylene-N$^+$(CH$_2$CH$_2$OH)$_3$, —($C_1$-$C_3$) alkylene-OR$^x$, —($C_1$-$C_4$)alkylene-CO$_2$R$^x$, —($C_1$-$C_4$) alkylene-CO$_2$N(R$^w$)R$^x$, —($C_1$-$C_4$)alkylene-C(=O) halogen, halo($C_1$-$C_3$)alkyl and —($C_1$-$C_4$) perfluoroalkylene-CO$_2$R$^x$;

$R^z$ is selected from the group consisting of —H, —($C_1$-$C_6$) alkyl, —(CH$_2$)$_3$—NH—C(NH$_2$)(=NH), —CH$_2$C (=O)NH$_2$, —CH$_2$COOH, —CH$_2$SH, —(CH$_2$)$_2$C (=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl);

each n is independently selected from the group consisting of 1, 2, 3 and 4;

provided that:
(i) each $R^1$ is other than 7-NR$^w$$_2$ or 7-OR$^w$;
(ii) each $R^1$ is other than 5- or 7-halogen, or 5- or 7-NO$_2$;
(iii) when n is 1, then $R^1$ is other than 6-NO$_2$, 6-Cl or 6-Br;

or a salt of such a compound.

2. A compound according to claim 1, wherein the compound is an isolated compound.

3. A compound according to claim 1 wherein R$^w$ is —H.

4. A compound according to claim 1 selected from the group consisting of:
6-fluoro-3-[(6-fluoro-2-oxochromen-3-yl)carbonyl] chromen-2-one; 6-iodo-3-[(6-iodo-2-oxochromen-3-yl)carbonyl]chromen-2-one; 6,8-dichloro-3-[(6,8-dichloro-2-oxochromen-3-yl)carbonyl]chromen-2-one; 6,8-dibromo-3-[(6,8-dibromo-2-oxochromen-3-yl)carbonyl]chromen-2-one; 6,8-difluoro-3-[(6,8-difluoro-2-oxochromen-3-yl)carbonyl]chromen-2-one; 6-chloro-8-bromo-3-[(6-chloro-8-bromo-2-oxochromen-3-yl) carbonyl]chromen-2-one; 8-nitro-3[(8-nitro-2-oxochromen-3-yl)carbonyl]chromen-2-one; 6-bromo-8-nitro-3-[(6-bromo-8-nitro-2-oxochromen-3-yl) carbonyl]chromen-2-one; 8-fluoro-3-[(8-fluoro-2-oxochromen-3-yl)carbonyl]chromen-2-one; 6-nitro-8-bromo-3-[(6-nitro-8-bromo-2-oxochromen-3-yl) carbonyl]chromen-2-one; 6,8-dinitro-3-[(6,8-dinitro-2-oxochromen-3-yl)carbonyl]chromen-2-one, and salts thereof.

5. A pharmaceutical composition comprising a pharmaceutically acceptable carrier and a compound or pharmaceutically acceptable salt thereof according to claim 1.

6. A method of treating an individual for a proliferative disorder comprising administering to said individual an effective amount of a compound according to claim 1.

7. A method according to claim 6 wherein the proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's Disease of the bone, fibrocystic disease of the breast, uterine fibroids, Peyronie's fibrosis, Dupuytren's fibrosis, restenosis, benign proliferative breast disease, benign prostatic hyperplasia, X-linked lymphoproliferative disorder, post-transplantation lymphoproliferative disorder, macular degeneration, retinopathies, proliferative vitreoretinopathy and non-cancerous lymphoproliferative disorders.

8. A method according to claim 6 wherein the proliferative disorder is cancer.

9. A method according to claim 8 wherein the cancer is selected from the group consisting of ovarian cancer, cervical cancer, breast cancer, prostate cancer, testicular cancer, lung cancer, renal cancer, colorectal cancer, skin cancer, brain cancer, and leukemia.

10. A method of treating an individual for a proliferative disorder comprising administering to said individual an effective amount of a composition according to claim 5.

11. A method of inducing apoptosis of tumor cells in an individual afflicted with cancer comprising administering to said individual an effective amount of a compound according to claim 1.

12. A method according to claim 11 wherein the tumor cells are selected from the group consisting of ovarian, cervical, breast, prostate, testicular, lung, renal, colorectal, skin and brain tumor cells.

13. A method of inducing apoptosis of tumor cells in an individual afflicted with cancer comprising administering to said individual an effective amount of a pharmaceutical composition according to claim 5.

14. A method of inhibiting growth of tumor cells in an individual suffering from a proliferative disorder comprising administering to said individual an effective amount of at least one compound according to claim 1.

15. A method of inhibiting growth of tumor cells in an individual suffering from a proliferative disorder comprising administering to said individual an effective amount of a pharmaceutical composition according to claim 5.

16. A method of treating an individual suffering from a viral infection, comprising administering to said individual an effective amount of at least one compound according to claim 1.

17. The method according to claim 16 wherein the virus is HIV.

18. A method of treating an individual suffering from a viral infection, comprising administering to said individual an effective amount of a pharmaceutical composition according to claim 5.

19. A process for preparing a compound according to claim 1, said process comprising the steps of:
(a) reacting a compound of formula IIA:

$$(R^1)_n \text{—} \underset{\text{OH}}{\overset{\text{CHO}}{\text{C}_6\text{H}_3}} \quad \text{IIA}$$

wherein:
each $R^1$ is independently selected from the group consisting of halogen, —C(=O)R$^y$, —NR$^w$$_2$, —N(R$^w$)C(=O) R$^y$, —N(R$^w$)CH(R$^z$)C(=O)R$^y$, —N(R$^w$)SO$_2$R$^y$, —NO$_2$, —CN, —OCH(R$^z$)C(=O)R$^y$, —OSO$_2$R$^y$—O ($C_1$-$C_4$)alkylene-CO$_2$R$^w$, —OP(=O)(OR$^w$)$_2$, —O($C_2$-$C_6$)alkylene-N(CH$_3$)$_2$, —P(=O)(OR$^w$)$_2$, —SO$_2$N(R$^w$) R$^x$, and —NHC(=NH)NHR$^x$;

R$^w$ is —H or —($C_1$-$C_8$)hydrocarbyl;

R$^x$ is —H, —($C_1$-$C_8$)hydrocarbyl or —C(=O)($C_1$-$C_8$)hydrocarbyl;

R$^y$ is selected from the group consisting of —H, —($C_1$-$C_8$) hydrocarbyl, —O($C_1$-$C_8$)hydrocarbyl, substituted phenyl, substituted heterocyclyl($C_1$-$C_3$)alkyl, heteroaryl ($C_1$-$C_3$)alkyl, —($C_2$-$C_{10}$)heteroalkyl, —($C_1$-$C_6$)

haloalkyl, —CH($R^z$)NH$R^x$, —N($R^w$)$R^x$, —($C_1$-$C_3$)alkyleneNH$_2$, —($C_1$-$C_3$)alkyleneN(CH$_3$)$_2$, —($C_1$-$C_3$)perfluoroalkyleneN(CH$_3$)$_2$, —($C_1$-$C_3$)alkyleneN$^+$($C_1$-$C_3$)$_3$, —($C_1$-$C_3$)alkylene-N$^+$(CH$_2$CH$_2$OH)$_3$, —($C_1$-$C_3$)alkylene-O$R^x$, —($C_1$-$C_4$)alkylene-CO$_2$$R^x$, —($C_1$-$C_4$)alkylene-CO$_2$N($R^w$)$R^x$, —($C_1$-$C_1$-$C_4$)alkylene-C(=O)halogen, halo($C_1$-$C_3$)alkyl and —($C_1$-$C_4$)perfluoroalkylene-CO$_2$$R^x$;

$R^z$ is selected from the group consisting of —H, —($C_1$-$C_6$)alkyl, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$CO$_2$H, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl) and —CH$_2$-(4-hydroxyphenyl); and n is 1, 2, 3 or 4;

with:

ROOC⌒C(=O)⌒COOR;

wherein:
R is —H or hydrocarbyl; and
(b) isolating a compound according to claim 1 from the reaction products.

* * * * *